US011145391B1

(12) United States Patent
Mirica

(10) Patent No.: US 11,145,391 B1
(45) Date of Patent: Oct. 12, 2021

(54) LONGITUDINAL CONDITION TRACKING SYSTEM AND METHOD

(71) Applicant: Health Vector LLC, Chestnut Hill, MA (US)

(72) Inventor: Dan M. Mirica, Chestnut Hill, MA (US)

(73) Assignee: Health Vector LLC, Chestnut Hill, MA (US)

(*) Notice: Subject to any disclaimer, the term of this patent is extended or adjusted under 35 U.S.C. 154(b) by 275 days.

(21) Appl. No.: 16/518,403

(22) Filed: Jul. 22, 2019

Related U.S. Application Data

(60) Provisional application No. 62/711,933, filed on Jul. 30, 2018.

(51) Int. Cl.
| | |
|---|---|
| *G16H 10/20* | (2018.01) |
| *G16H 50/20* | (2018.01) |
| *H04L 9/06* | (2006.01) |
| *G06F 16/182* | (2019.01) |
| *G16H 10/60* | (2018.01) |

(52) U.S. Cl.
CPC ......... *G16H 10/20* (2018.01); *G06F 16/1824* (2019.01); *G16H 10/60* (2018.01); *G16H 50/20* (2018.01); *H04L 9/0637* (2013.01); *H04L 2209/38* (2013.01)

(58) Field of Classification Search
CPC .......... G06Q 50/22–24; G06F 16/1824; G06F 21/62; G06F 11/3476; G06F 16/2358; G06F 17/40; G06F 2221/0775; G06F 16/27; H04L 9/0637; H04L 2209/38
See application file for complete search history.

(56) References Cited

U.S. PATENT DOCUMENTS

| 2017/0161439 A1* | 6/2017 | Raduchel | H04W 12/06 |
| 2018/0211058 A1* | 7/2018 | Aunger | H04L 63/0428 |
| 2019/0027237 A1* | 1/2019 | McFarlane | H04L 9/3247 |

FOREIGN PATENT DOCUMENTS

| EP | 3 511 851 A1 * | 1/2018 | G06F 21/33 |

* cited by examiner

*Primary Examiner* — Robert W Morgan
*Assistant Examiner* — Emily Huynh
(74) *Attorney, Agent, or Firm* — Morse, Barnes-Brown & Pendleton, P.C.; Sean D. Detweiler, Esq.

(57) ABSTRACT

A system and method for coordinating cooperative diagnosis construction, decreasing diagnostic error, reducing delays and repetition in performing tasks, and improving application of data gathering devices through structured data tracking of symptoms, diagnoses, conditions and records using encrypted, event-based blockchain ledgers distributed throughout a network of processors. Symptom and diagnosis devices are used to collect participant data. Data is encrypted and used to generate a secure chain of decentralized ledger blocks. The secure chain is stored in a network of secure processing devices. Data access is controlled by a gatekeeper. Structured data blocks are integrated, creating a comprehensive digital record that may be shared without sacrificing control. Pathology collections are generated from integrated data. Interfaces are used to provide reports and directives to allow participants to leverage data and perform tasks that were heretofore unavailable while simultaneously improving privacy, security, usability and accessibility of participant conditions, events and data.

4 Claims, 18 Drawing Sheets

US 11,145,391 B1

LONGITUDINAL CONDITION TRACKING SYSTEM AND METHOD

CROSS-REFERENCE TO RELATED APPLICATION(S)

This application claims priority to, and the benefit of, U.S. Provisional Application No. 62/711,933, filed Jul. 30, 2018, for all subject matter common to both applications. The disclosure of said provisional application is hereby incorporated by reference in its entirety.

FIELD OF THE INVENTION

The present invention relates to systems and methods for integrated longitudinal condition tracking suitable for coordinating cooperative diagnosis construction, decreasing diagnostic error, increasing relevant data integration, reducing delays and repetition in performing tasks, increasing reliable documentation for analysis and review, strengthening the partnership between patient and physician participants, co-writing the diagnosis narratives and improving coordination of participants and data gathering devices by effectively managing structured and unstructured data for symptoms, diagnoses, conditions and records using encrypted, event-based blockchain ledgers distributed throughout a network of processors. In particular, the present invention relates to systems and methods that collect, authenticate, store and track participant data, where all components and aspects of participant data can be integrated into a comprehensive view of a digital health record using a secure chain of decentralized ledger blocks that may be shared for specific purposes using interfaces to provide reports and directives to allow participants to leverage data and perform tasks that were heretofore unavailable, while simultaneously improving privacy, security, usability and accessibility of participant conditions, events, and data.

BACKGROUND

Generally, electronic records provide the opportunity to collect, transfer, store, aggregate, integrate, research, track, and manage record data far more efficiently than prior record keeping formats. In theory, using electronic records should vastly improve data management leading to superior organization, processing, timeliness, assessment and usefulness of data in a variety of industries and sectors, including healthcare. In practice, however, this technology experiences various shortcomings. Health care professionals acquiring data operate independently with incompatible systems and data management procedures, leading to persistent data fragmentation across specialties, geographies, and time periods. Regulatory schemes, including privacy regulations, and other legal requirements impede the free flow of information. Proliferation of data custodians lack of cooperation between record keeping entities, and non-standard records, without control by those most impacted by the records, minimize the functionality, consolidation and usability of data, resulting in incomplete data sets, lack of infrastructure and data structures, slow record aggregation, increased threats to privacy and data security, and numerous delays associated with attempts to communicate symptoms to medical professionals, inquiries related to scheduling appointments with healthcare providers, and pre-appointment activities related record maintenance or verification of symptoms or medical history. Moreover, in the context of healthcare data, missing or inaccurate records regarding allergies, prescribed medications, and existing conditions can have life threatening consequences when not considered pursuant to courses of treatment.

SUMMARY

There is a need for an integrated longitudinal condition tracking system and method that allows electronic record keeping to overcome current difficulties related to isolated, incomplete, fragmented data managed by custodians incapable of efficient cooperation and instead produce a comprehensive resource that can easily be used by a variety of participants to take advantage of more of the functionalities electronic recordkeeping offers. The present invention is directed toward further solutions to address this and other needs, in addition to having other desirable characteristics and benefits that will be appreciated by one of skill in the art upon reading the present specification. Specifically the integrated longitudinal condition tracking system and method improve data management through structured data tracking of active symptom data linking to diagnostic data so that all components and aspects of health data can be integrated into a comprehensive digital health record, thereby decreasing diagnostic error, increasing relevant data integration, reducing delays and repetition in performing tasks, increasing reliable documentation for analysis and review, and improving coordination of participants and data gathering devices by effectively managing structured and unstructured data for symptoms, diagnoses, conditions and records using encrypted, event-based blockchain ledgers distributed throughout a network of processors. The system and method strengthens physician-patient relationships and improves overall quality of care by providing symptom data to healthcare providers in a timely and structured format. In this way patterns identified with risks to participants 102 can be discovered by the system 100 in a timely fashion and medical assistance can be scheduled without the delays associated with communicating symptoms to medical professionals, inquiries related to scheduling appointments with healthcare providers, or pre-appointment activities related record maintenance or verification of symptoms or medical history. The participant has control to share all data or parts thereof with authorized healthcare providers for a limited time and a specific purpose. Healthcare providers and insurers can be granted a comprehensive view of the participant's digital health record. All information is encrypted in a private blockchain ledger comprising a secure chain of decentralized ledger blocks. This allows the participant, or gatekeeper thereof, to give permission to network participants to view some or all of the records in the secure chain of decentralized ledger blocks. This integrated longitudinal condition tracking technology departs from conventional data management practices and systems that isolate data and do not generate data that may be integrated, and the technology fundamentally changes procedures for data acquisition, storage and providing improvements over existing systems that yield near immutable, private, secure, data resources. This technology imparts capabilities for tracking symptom data and diagnosis data together, using structured data to further map events and patterns thereof, and compiling unique aggregations of integrated data from disparate sources to yield pathology collections, all of which were not possible with conventional systems. The invention represents a technological advancement in the form of a system and method for providing, on a user device with a graphical user interface, the practical application of a heretofore previously unavailable system that enables a process to aggregate, integrate by linking, present, and analyze a comprehensive, real-time updating digital health record that remains current and updated but preserves prior medical data without unnecessary reliance on medical professionals to initiate cooperation (compliant with applicable laws, regulations, and safeguards) between care providers and/or record keepers. The integration of structured data stored within secure chain of decentralized ledger blocks residing in a network of secure processing devices so as to generate pathology collections in real time also constitutes a significant improvement in user interfaces used for data management and tracking. The invention provides a combination of additional elements including storing information (using e.g. secure processing devices), providing remote access over a network using a gatekeeper, linking relevant related data or sets thereof, compiling and curating reports and pathology collections, converting updated information that was input by e.g. a user in a non-standardized form to a standardized, structured data format, automatically generating a message whenever updated information is stored, transmitting the message to all of the relevant blocks in one or more secure chains that are then used to notify users, and automation of appointment, note, notation, message, notification, action, follow up, diagnostic event or treatment recommendation protocol generation based on observed patterns in data. The invention integrates medical and healthcare records, symptoms input from a user, symptom and medical data generally, diagnostic data from a diagnosis acquisition device, and/or institutional data, as well as organizing human activity, providing a practical application wherein the additional elements recite a specific improvement over prior art systems by allowing remote users to share information in real time in a standardized format regardless of the format in which the information was input by the user. The additional elements further include linking and making accessible data that was previously unavailable to certain users or participants by securing access to updateable but immutable records that are encrypted and restricted while able to be integrated and aggregated to provide pathology collections and digital health records for a patient lifetime health record where events from birth to end of life are stored in an integrated and comprehensive fashion along with additional data such as timestamp and time scale data that can be used to organize and track the event data. The systems and methods empower the user by providing control and information in a technologically implemented improvement to existing processes for record generation, access, management, and transformation, specifically integrated longitudinal secure chain data tracking that provides multiple layers of data encryption, that is traditionally controlled by external parties, namely various health care providers that cannot or do not cooperate efficiently. The systems and methods provide immediate, real-time, substantiation of actions performed related to the health care of a user that confirm completion and create a record validating that action for cross-referencing and linking to other health care data, which increases coordination between system participants and documentation often required in the medical setting, and this type of integrated verification can also serve to minimize the risk for data breach, misdiagnosis or other diagnostic error, recordkeeping errors, delays and repetition in performing tasks. Thus numerous practical applications and benefits result from the technology and process of the present invention, wherein the GUI of the invention further provides a tool for managing care that integrates a number of diverse computing and mental processes into a practical application with steps transforming protected and encrypted compiled longitudinal data into an interactive format to guide health record management, that cannot be not practically performed in a human mind that does not have the facility to coordinate digital records form the various digital record generating sources while acquiring corroborative data, parsing that data, aligning, linking, and aggregating that data, then summarizing that data in a comprehensive interactive record that can be explored at different levels of granularity to assess patterns and trends in health care records related to a user.

In accordance with example embodiments of the present invention, an integrated longitudinal condition tracking system is provided for creating a tool to effectively generate and manage a comprehensive, integrated participant data history that can be flexibly analyzed and shared with other participants while maintaining security and privacy for the subject source of the data. A diagnosis acquisition device performs diagnosis acquisition tasks related to a participant. The diagnosis acquisition device generates an encrypted diagnosis event block that corresponds to each of the diagnosis acquisition tasks performed and stores diagnosis data in structured data units. A symptom collecting device captures symptom information related to a participant. The symptom collecting device generates an encrypted symptom event block that stores symptom data in structured data units. A secure chain of decentralized ledger blocks store, verify, and link decentralized chains of encrypted diagnosis event blocks and encrypted symptom event blocks for a participant based on structured data. This architecture makes the encrypted diagnosis event blocks and encrypted symptom event blocks of the secure chain immutable and secure. A gatekeeper manages both encryption and access to the secure chain based on authority granted to the gatekeeper and recorded in the secure chain. The gatekeeper possesses authority to grant and deny access to subsets of the secure chain by participants, and access is controlled by configuring sets of structured data. A network of secure processing devices store secure chains of decentralized ledger blocks comprising encrypted diagnosis event blocks and encrypted symptom event blocks from participants. The network of secure processing devices perform data integration tasks by migrating along longitudinal paths of the secure chain, parsing decentralized ledger blocks using structured data embedded in the decentralized ledger blocks. The structured data embedded in the decentralized ledger blocks control access to encrypted diagnosis event blocks and encrypted symptom event blocks based on access granted by the gatekeeper. The network of secure processing devices generate pathology collections of encrypted diagnosis event blocks and encrypted symptom event blocks based on sets of parsed structured data. These pathology collections are configured based on input from a participant, subject to access granted to the participant by the gatekeeper. The system provides at least one interface to supply participants with reports and create, using input, action directives, wherein the reports and action directives uniquely aggregate data from the pathology collections.

In accordance with aspects of the present invention, the integrated longitudinal condition tracking system can include a diagnosis acquisition device comprising one or more of the group consisting of an examination device, laboratory equipment, diagnostic equipment, imaging equipment and an authorized computing device configured to receive and store diagnostic data input from a health care professional. A diagnosis acquisition device may digitize diagnostic data and upload the diagnostic data to the network of secure processing devices.

In accordance with aspects of the present invention, the integrated longitudinal condition tracking system can include a symptom collecting device comprising one or more of the group consisting of an imaging device, a recording device, self-administered diagnostic instruments and an authorized patient computing device configured to receive and store symptom data input by a participant. A symptom collecting device can digitize symptom data and upload the symptom data to the network of secure processing devices.

In accordance with aspects of the present invention, the integrated longitudinal condition tracking system can include at least one participant that comprises one or more of the group consisting of a patient, an authorized patient relative, an authorized physician, an authorized researcher, an authorized healthcare worker, and an authorized health insurance data custodian.

In accordance with aspects of the present invention, the structured data in the system can comprise one or more of the group consisting of symptom name data, additional accompanying symptom data, date and time data, participant note data, problem and chronic condition links, alleviating factor data, aggravating factor data, frequency data, duration data, perception data, description data, trend data, environmental factor data, weather data and history data.

In accordance with aspects of the present invention, the integrated longitudinal condition tracking system can comprise encrypted diagnosis event blocks and encrypted symptom event blocks that are encrypted with a private key unique to each secure chain and belonging to the gatekeeper that is a component of a public key, private key infrastructure, wherein modification may only be accomplished through access granted by the private key.

In accordance with aspects of the present invention, the integrated longitudinal condition tracking system can comprise at least one action directive that comprises an appointment generated and scheduled from data derived from the pathology collections linking encrypted symptom event blocks to appointment attributes set by a participant, and wherein once set, the action directive generates an encrypted diagnosis event block.

In accordance with aspects of the present invention, each of the decentralized ledger blocks in the secure chain of decentralized ledger blocks can comprise a hash of a previous block in the secure chain and hashes related to links to other blocks derived from structured data associated with the decentralized ledger blocks.

In accordance with aspects of the present invention, the integrated longitudinal condition tracking system can further comprise an interface wherein the participant can enter data into network of secure processing devices to create pathology collections that are configured based on input from a participant, thereby integrating diagnosis data and symptom data according to data entered by the participant.

In accordance with aspects of the present invention, the integrated longitudinal condition tracking system can be configured to use the network of secure processing devices to add additional data, define structured data, and limit access to the secure chain based on privacy restrictions and security restrictions input into the network of secure processing devices by authorized participants.

In accordance with aspects of the present invention, the decentralized ledger blocks can further comprise one or more of the group consisting of medications, immunizations, laboratory tests and results, procedures, problems and chronic conditions, allergies, medical visits, and appointments, wherein corresponding links are generated for each of the decentralized ledger blocks to form a condition based set.

In accordance with aspects of the present invention, the interface can be further configured to allow the participant to review the decentralized ledger blocks in a set over an input time period and add links further integrating the decentralized ledger blocks, and the interface can be further configured to allow the participant to share pathology collections, decentralized ledger blocks and structured data thereof with another participant. The interface can also be configured to allow the participant to view pathology collections, decentralized ledger blocks and structured data thereof for an aggregation of anonymized participants, wherein aggregation and anonymization are controlled by structured data in the secure chain.

In accordance with aspects of the present invention, the interface of the system is further configured to allow the participant to view offers presented by other participants based on pathology collections, decentralized ledger blocks and structured data thereof for an aggregation of anonymized participants, wherein aggregation and anonymization are controlled by structured data in the secure chain.

In accordance with example embodiments of the present invention, a method is provided for integrated longitudinal condition tracking. As part of said method, at least one diagnostic acquisition device performs diagnostic acquisition tasks related to a participant and generates an encrypted diagnosis event block that corresponds to each of the diagnosis acquisition tasks performed and stores diagnosis data in structured data units therein. Additionally, a symptom collecting device captures symptom information related to a participant and generates, using the symptom collecting device, an encrypted symptom event block that stores symptom data in structured data units therein. The method uses a secure chain of decentralized ledger blocks to verify, store, and link decentralized chains of encrypted diagnosis event blocks and encrypted symptom event blocks for a participant based on the structured data, which renders the encrypted diagnosis event blocks and encrypted symptom event blocks of the secure chain immutable and secure. A gatekeeper manages encryption and access to the secure chain based on authority granted to the gatekeeper and recorded within the secure chain. The gatekeeper possesses authority to grant and deny access to subsets of the secure chain by one or more participants, wherein access is controlled by configuring sets of structured data. A network of secure processing devices stores each of the secure chains of decentralized ledger blocks comprising encrypted diagnosis event blocks and encrypted symptom event blocks received from participants via diagnostic acquisition devices and diagnosis acquisition devices 110. The method uses the network of secure processing devices to perform data integration tasks, wherein the network of secure processing devices processes data, migrates along longitudinal paths of the secure chain, and parses decentralized ledger blocks using structured data embedded in the decentralized ledger blocks. The structured data embedded in the decentralized ledger blocks controls access to encrypted diagnosis event blocks and encrypted symptom event blocks based on access granted by the gatekeeper. The method, using a network of secure processing devices, generates pathology collections of encrypted diagnosis event blocks and encrypted symptom event blocks based on sets of parsed structured data. The pathology collections are configured based on input from a participant, subject to access granted to the participant by the gatekeeper. The method uses an interface to supply participants with reports and create, using input, action directives, wherein the reports and action directives uniquely aggregate data from the pathology collections.

In accordance with aspects of the present invention, the interface of the method is further configured approve access to pathology collections, unstructured data and structured stored in decentralized ledger blocks and the network of secure processing devices related to participants participating in a digital health marketplace based on submissions of at least one requesting participant. The approving can provide the at least one requesting participant access to a network portal displayed using an interface of a system for integrated longitudinal condition tracking; receive, from the at least one requesting participant accessing the network portal using the interface, a request to set up a research project offer submission on digital health marketplace residing within the network of secure processing devices; receive, from the at least one requesting participant accessing the network portal using the interface, identification information linking the research project offer submission to structured data stored in a secure chain of decentralized ledger blocks and the network of secure processing devices belonging to the requesting participant; receive, from the at least one requesting participant, research project parameters for setting up a research project designed by one or more requesting participants, wherein research project parameters comprise inclusion criteria, exclusion criteria, threshold criteria, time criteria, criteria weighting, compensation data for participants, compensation account data, and offer data to be presented to participants including type of research and research goal; store research project parameters and the request to set up a research project offer submission in the network of secure processing devices, wherein project parameters are encrypted; receive, from the at least one requesting participant, evidence of approval, wherein evidence of approval comprises uploading to the network of secure processing devices, using the interface, one or more of the group consisting of internal approval, regulatory approval, and prior network administrator approval; review, by the network of secure processing devices and network administrators, the stored research project parameters, evidence of approval, network data and laws, rules and regulations governing research projects; provide to the at least one requesting participant, by the interface, an approval decision; transfer funds, based upon the approval decision and research project parameters, using compensation account data, into an escrow account managed by the network of secure processing devices to be distributed by the network of secure processing devices to participants completing milestones in research project participation; publish, the research project offer in the digital health market place using the interface and the network of secure processing devices, and storing the research project offer in a database related to the digital health marketplace that is indexed and searchable; and update structured data, encrypted blocks, access controls, access privileges, privacy restrictions and security restrictions stored in the secure chain of decentralized ledger blocks and the network of secure processing devices managed the network, and network administrators based on the approval decision.

In accordance with aspects of the present invention, the interface of the method is further configured to receive, from a participant using an interface of a system for integrated longitudinal condition tracking, a selection of one of the group consisting of non-participation in a digital health marketplace, consent to participate in browsing services allowing said participant to browse offers from available active research projects published on the digital health marketplace, and consent to search space services for matching to receive prequalified targeted offers from available active research projects; wherein participation in browsing services comprises the participant electing when to engage with said offers stored in a database related to the digital health marketplace to determine whether research project parameters match structured data of the participant; wherein search space services anonymize participant structured data, aggregate participant structured data and make participant structured data available to requesting participants for matching to receive prequalified targeted offers from available active research projects according to submitted research project parameters; wherein research projects comprise one or more of the group consisting of anonymous retrospective studies, anonymous prospective surveillance studies, anonymous one-time surveys or non-anonymous virtual clinical research and non-anonymous in-person clinical research; update structured data, encrypted blocks, access controls, access privileges, privacy restrictions and security restrictions stored in the secure chain of decentralized ledger blocks and the network of secure processing devices managed by the gatekeeper, the network, and network administrators based on the selection made by the participant; and configure the interface to display a set of data related to the digital health marketplace, browsing services, and search space services authorized by the selection made by the participant.

In accordance with aspects of the present invention, the interface of the method is further configured to receive, from at least one participant, a request to match research project parameters of a research project offer to a subset of the structured and unstructured data stored in a secure chain of decentralized ledger blocks belonging to a potential participant that the at least one participant is authorized to access based upon the structured data, encrypted blocks, access controls, access privileges, privacy restrictions and security restrictions stored in the secure chain of decentralized ledger blocks and the network of secure processing devices managed by the gatekeeper, the network, and network administrators; execute action directives anonymizing data and aggregating data from pathology collections of the participant subject to the request to match, according to the research project parameters, migrating along longitudinal paths of the secure chain, parsing decentralized ledger blocks using structured data embedded in the decentralized ledger blocks, performing data integration, and collecting relevant pathology collections; generate a score indicating an aggregated match of the potential participant to research project parameters calculated based on pathology collections; present, via the interface, a score assessing the volunteer participant, to the at least one participant.

In accordance with aspects of the present invention, the interface of the method is further configured to insert research project parameters, input by at least one requesting participant, into agreement terms; convert structured data stored in pathology collections into agreement terms by insertion of the structured data and related action directives, input by at least one requesting participant, into agreement data stored in the network of secure processing devices; parse, structured data in the secure chain of decentralized ledger blocks and identifying structured data that do not match the research project parameters input into action directives, wherein prior executed agreements and prior participation in research projects is evaluated; approve, using input by requesting participant, a final form of agreement terms; present, using at least one interface, the final form of agreement terms to two or more participants including the at least one requesting participant and the at least one potential participant; execute, the agreement between two or more participants, wherein each respective participant supplies consent and acceptance by input into the interface and application thereby transferring data to the network of secure processing devices; modify, using structured data stored in the newly generated agreement terms blocks, structured data, encrypted blocks, access controls, access privileges, privacy restrictions and security restrictions stored in the secure chain of decentralized ledger blocks and the network of secure processing devices managed by the gatekeeper, the network, and network administrators, yielding access to additional structured data contained within the secure chain of decentralized blocks comprising the digital health record of the potential participant; and store, using one or more additional decentralized ledger blocks residing in the network of secure processing devices, the agreement terms, consent and acceptance between two or more participants, thereby adding to the secure chain of decentralized ledger blocks and creating an additional immutable record for subsequent integration and tracking, wherein data are encrypted, immutable, and stored in distributed format in the secure chain of decentralized ledger blocks representing a digital health marketplace.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
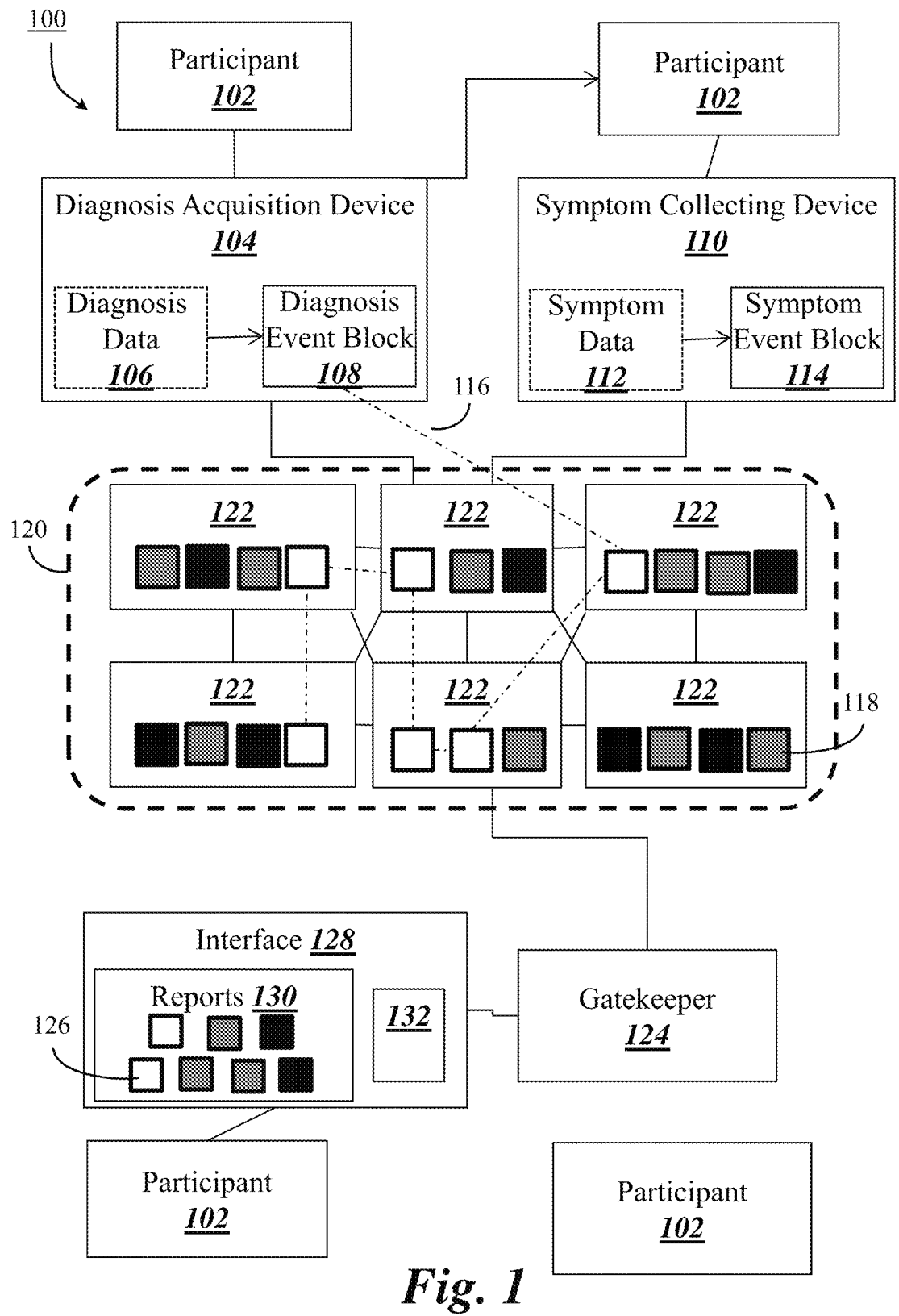
FIG. 1 is an illustrative diagram of an example embodiment of a system for performing one or more functions of the embodiments of the present invention.

An illustrative embodiment of the present invention relates to an integrated longitudinal condition tracking system and method that uses a network of secure processing devices and acquisition devices to collect data then generates from that data a secure chain of decentralized ledger blocks that comprise a comprehensive, real-time updating digital health record that also serves to integrate data from various sources and aggregate data into pathology collections presented for review and analysis in reports or subsequently used as part of management of a digital health marketplace. The integrated longitudinal condition tracking system decrease diagnostic error through structured data tracking of active symptom data and linking to diagnostic data in a participant's secure chain, digital health record, or external patient medical records. All components and aspects of health data can be integrated into the digital health record. The participant can share all or parts of the data with healthcare providers for a limited time and a specific purpose. Authorized healthcare providers and insurers can become additional participants and have access to a comprehensive view of the participant's digital health record. All information is encrypted in the cloud residing on a private network of secure processing devices and a private blockchain ledger in the form of a secure chain of decentralized ledger blocks. The secure chain of decentralized ledger blocks is managed by the system administrator and is run on a closed network with participating patients, healthcare providers, payers, companies, and other entities that subscribe and become participants. This allows each participant to give permission to network participants to view some or all of the records in the blockchain ledger. The private blockchain significantly increases security and safety for participant information. The participant can use the system to participate in a digital health marketplace and choose to participate in anonymous and non-anonymous research projects and get paid. The selection data is fully secure, encrypted and available only to the participant after a smart agreement is executed and entered. The smart agreement is stored on the secure chain related to the marketplace in an immutable format and fully encrypted.

FIGS. 1 through 18, wherein like parts are designated by like reference numerals throughout, illustrate an example embodiment or embodiments of an integrated longitudinal condition tracking system and method that uses secure chains of decentralized ledger blocks to link and organize structured data that can be used as a tool to effectively generate and manage a comprehensive, integrated participant data narrative history that can be flexibly analyzed and shared with other participants while maintaining security and privacy for the subject source of the data, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed in a manner still in keeping with the spirit and scope of the present invention.

FIG. 1 depicts an overview of the components and configuration of an integrated longitudinal condition tracking system 100. An aspect of the invention provides a diagnosis acquisition device 104 that performs diagnosis acquisition tasks related to a participant 102. The diagnosis acquisition device 104 generates an encrypted diagnosis event block 108 that corresponds to each of the diagnosis acquisition tasks performed and stores diagnosis data in structured data units. A symptom collecting device 110 captures symptom information related to a participant 102. The symptom collecting device 110 generates an encrypted symptom event block 114 that stores symptom data 112 in structured data units. A secure chain 116 of decentralized ledger blocks 118 store, verify, and link decentralized chains of encrypted diagnosis event blocks 108 and encrypted symptom event blocks 114 for a participant 102 based on structured data. This architecture makes the encrypted diagnosis event blocks 108 and encrypted symptom event blocks 114 of the secure chain 116 immutable and secure. A gatekeeper 124 manages both encryption and access to the secure chain 116 based on authority granted to the gatekeeper 124 and recorded in the secure chain 116. The gatekeeper 124 possesses authority to grant and deny access to subsets of the secure chain 116 by participants 102, and access is controlled by configuring sets of structured data. A network 120 of secure processing devices 122 store secure chains 116 of decentralized ledger blocks 118 comprising encrypted diagnosis event blocks 108 and encrypted symptom event blocks 114 from participants 102. The network 120 of secure processing devices 122 perform data integration tasks by migrating along longitudinal paths of the secure chain 116, parsing decentralized ledger blocks 118 using structured data embedded in the decentralized ledger blocks 118. The structured data embedded in the decentralized ledger blocks 118 control access to encrypted diagnosis event blocks 108 and encrypted symptom event blocks 114 based on access granted by the gatekeeper 124. The network 120 of secure processing devices 122 generate pathology collections 126 of encrypted diagnosis event blocks 108 and encrypted symptom event blocks 114 based on sets of parsed structured data. These pathology collections 126 are configured based on input from a participant 102, subject to access granted to the participant 102 by the gatekeeper 124. The system 100 provides at least one interface 128 to supply participants 102 with reports 130 and create, using input, action directives 132, wherein the reports 130 and action directives 132 uniquely aggregate data from the pathology collections 126. As used herein, a "gatekeeper" 124 means an authority designated in the system 100 to control access and authorization with respect to a particular participant's secure chain 116 of decentralized ledger blocks 118 residing within the network 120 of secure processing devices 122, resulting digital health record, or data derived therefrom. Upon subscription or execution of a relevant smart agreement, a gatekeeper 124 is designated within the data first entered into the initial ledger blocks of the secure chain 116 for the newly subscribed participant 102. For example, without limiting the invention herein, the gatekeeper may serve as the primary controller of information regarding one or more participants 102. In the case of a typical adult patient subscribing as a participant 102, that adult patient participant 102 would be designated as gatekeeper 124 of the data corresponding to that person's own secure chain 116 and digital health record. In the case of a minor individual or incapacitated individual, or other person requiring guardianship (such as a senior citizen with cognitive disabilities), the parent or legal guardian would be designated as the gatekeeper for the other individuals' secure chain 116 and digital health record, so this parent or guardian would be able to manage health decisions including with respect to use of data regarding the participant 102. A gatekeeper may also be a mechanism or device which controls access and coordinates encryption of exchanged data, where gatekeeper components may include: DHR App Encryption Layer, DHR Exchange Encryption Layer, DHR Certificate Authority, DHM Certificate Authority, DHM Portal and Exchange permissions, DHR Secure Perimeter Network encryption and security, DHM Secure Perimeter Network encryption and security. A gatekeeper may also be a default set of rules and protocols governing data privacy and sharing protocols, stored in the system 100 and used in the event no other entity is designated, or a gatekeeper may be the combination of a parent or guardian and processors enforcing rules and protocols.

As used herein, a "participant" 102 means any entity that supplies data to, accesses data from, or subscribes to participate in using the integrated longitudinal condition tracking system 100 and method 600 of the invention disclosed herein. In certain embodiments, the participant 102 is a subject or patient from which diagnostic data 106 is obtained. Conversely, in other embodiments, the participant 102 is not the source of diagnostic data, but is another entity entirely. In accordance with certain aspects of the present invention, the integrated longitudinal condition tracking system 100 may include at least one participant 102 that comprises one or more of the group consisting of a patient, an authorized patient relative, an authorized physician, an authorized researcher, an authorized healthcare worker, and an authorized health insurance data custodian. In other embodiments, a participant 102 may be any other entity subscribing to participate in using the system 100.

In accordance with aspects of the present invention, the integrated longitudinal condition tracking system 100 can include a diagnosis acquisition device 104 comprising one or more of the group consisting of an examination device, laboratory equipment, diagnostic equipment, imaging equipment, and may additionally comprise an authorized computing device configured to receive and store diagnostic data input from a health care professional. A diagnosis acquisition device 104 performs diagnostic acquisition tasks that identify or measure a condition or quantity related to at least one participant 102. A diagnosis acquisition device 104 may digitize diagnostic data of various forms or formats and upload the diagnostic data to the network 120 of secure processing devices 122.

Parsing in the secure chain blockchain is done in conjunction with the network of secure processing devices operating as an encrypted data farm. The data contents stored in the DHR EDF (Encrypted Data Farm) is linked to the participant blockchain with a unique user identifier to ensure anonymity and security of health information. One of ordinary skill in the art will be readily aware of known techniques for parsing data of a block chain. Data integration and creation of pathology collections comprises basic queries and commands including: Medicine link to problems and chronic conditions; Appointment link to notes; Symptoms link to weather and environmental data; Medical visit link to notes, problems and chronic conditions; Symptoms, Immunizations, Lab Tests, Procedures link to Problems and Chronic Conditions; Longitudinal link for all entries based on timeline; Billing codes link to medical visits, diagnostics, medications and all other note types. Establishing links between DHR elements may be accomplished using many to many relationships. User queries may be based on any element or elements in the DHR leading to the resulting report including all linked and related information. Interfaces used in various example embodiments include: an Application interface where the user can input and retrieve DHR information from one or more encrypted data farms and one or more blockchains, as well as network partners data, wherein the Application interface may also comprise a graphical user interface (GUI) that presents collections, reports or records based on user input, integrating and aggregating data while preserving anonymity, isolating various users and participants using a gatekeeper 124 providing selective, programmable controlled access to EDF or secure block chain resources (including analysis from pathology collections for e.g. research project data) based on verified or authorized participant or user identity conferring appropriate access credentials residing within a particular participant's secure chain 116 of decentralized ledger blocks 118, further residing within the network 120 of secure processing devices 122; application programming interfaces (APIs) where the user initiates data exchange with external sources like mobile, fitness or medical devices, patient portals, healthcare providers and payers, employer portals, other IoT devices; Interfaces between the DHR research offers and payment engine and DHM research project builder and processor to ensure complete separation of user identity and health information and research entity during the offer selection process; Interfaces between DHR payment processing engine and DHM payment engine to ensure secure payment and maintain user anonymity and protect identity and integrity of user health information; and Interfaces between DHM components (Portal and Exchange) and research entities.

Figure 2:
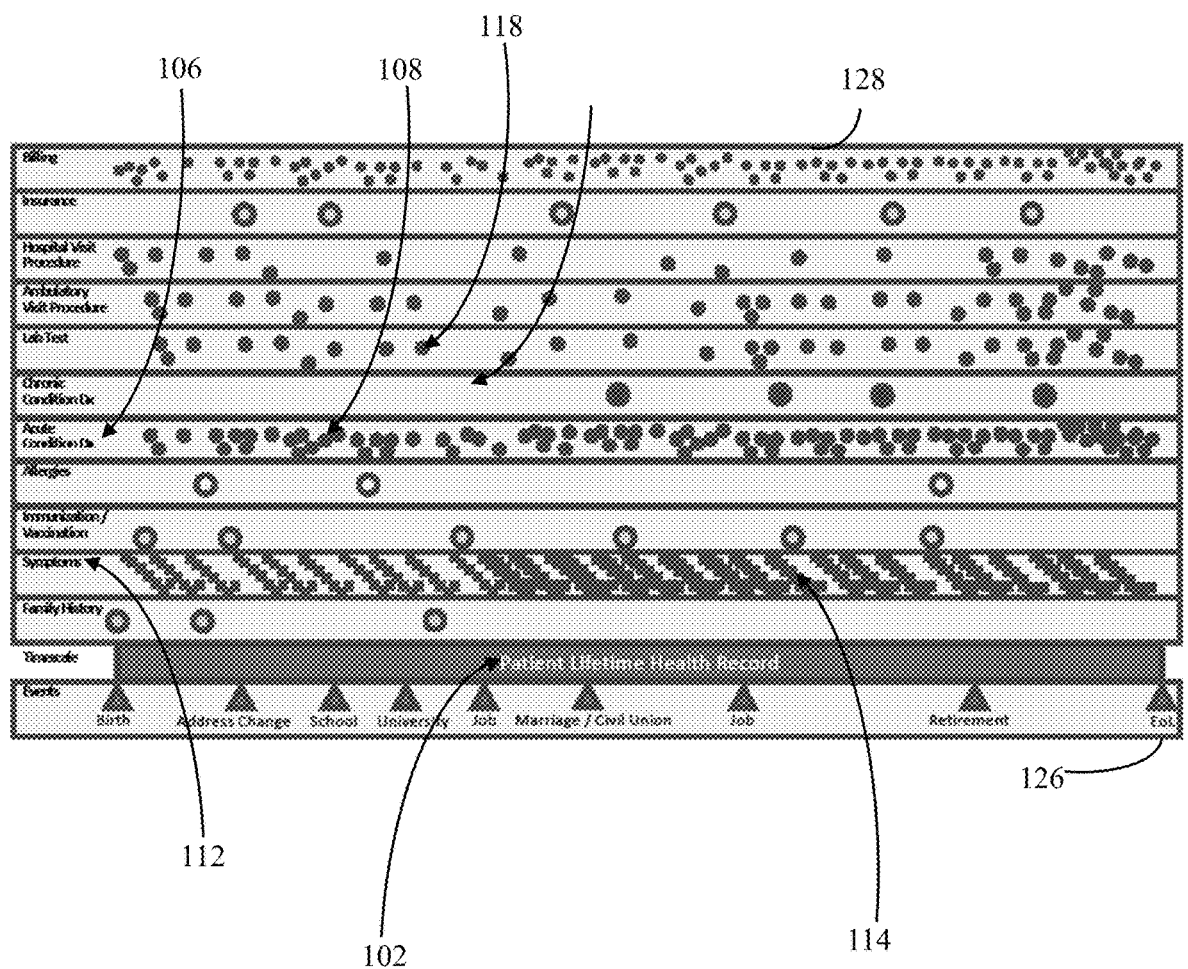
FIG. 2 is an illustration of the structure of collected participant data.
Figure 3:
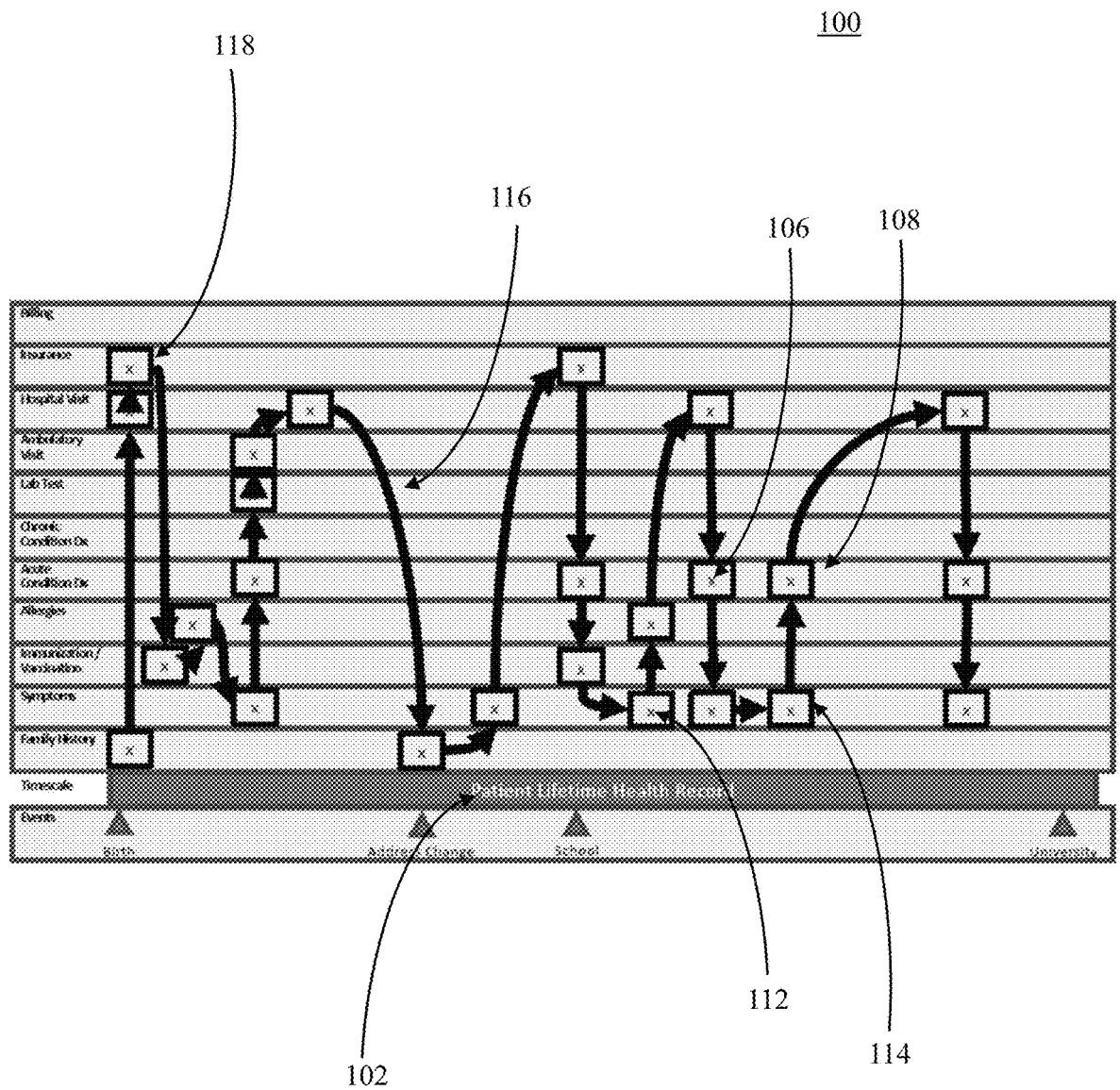
FIG. 3 is a diagram of the block chain storing collected participant data.

FIG. 2 depicts an illustrative embodiment of the system 100 wherein structured data, corresponding to a distribution of decentralized ledger blocks 118 comprising encrypted diagnosis event blocks 108 and encrypted symptom event blocks 114, generate and map out a digital health record (accessible via GUI) created using the integrated longitudinal condition tracking system 100. Decentralized ledger blocks 118 store structured data and event data, that may be in the form of structured data, corresponding to one or more of the group consisting of medication prescriptions and/or administrations, immunizations and/or vaccinations, laboratory tests and/or results, procedures, problems and/or chronic conditions, allergies, medical visits, and appointments. Corresponding links are generated for each of the decentralized ledger blocks 118 to form a condition based set. A digital health record may comprise one or more condition based sets. A digital health record may store data representative of or related to at least one participant 102. A digital health record may comprise one or more secure chains 116 of decentralized ledger blocks 118. In FIG. 3, the decentralized ledger blocks 118 depicted comprise event data corresponding to both diagnosis data 106 stored within encrypted diagnosis event blocks 108, and symptom data 112 stored within encrypted symptom event blocks 114, wherein the depicted events represent specific categories of structured data including billing, insurance, hospital visit procedures, ambulatory visit procedures, lab tests, problem and/or chronic condition diagnosis, acute condition diagnosis, allergies, immunizations and/or vaccinations, symptoms, and family history. The digital health record forms a patient lifetime health record where events from birth to end of life are stored in an integrated and comprehensive fashion along with additional data such as timestamp and time scale data that can be used to organize and track the event data. FIG. 3 further depicts how the structured event data forming a digital health record for a participant 102, as depicted in FIG. 2, is constructed over the lifetime of that participant 102 by sequentially linking one or more secure chains 116 of decentralized ledger blocks 118. Structured data and event data for each new event is recorded in a newly generated instance of one of the decentralized ledger blocks 118, which uses structured data found in the existing secure chain 116 together with system 100 data and participant 102 data to link appropriately to the secure chain 116, including by propagating data from the existing secure chain 116 that is incorporated into the data stored in the newly generated block, thus growing the secure chain 116 of decentralized ledger blocks 118. FIG. 3 also depicts each block corresponding to the same specific categories of structured data as represented in FIG. 2, including billing, insurance, hospital visit procedures, ambulatory visit procedures, lab tests, problem and/or chronic condition diagnosis, acute condition diagnosis, allergies, immunizations and/or vaccinations, symptoms, and family history.

Thus each participant has a blockchain which contains digital health records distributed over individual blocks. The only way to establish relationships between records from different patients is based on each individual user consent to participate in a study. Each participant can join one or more research studies and anonymized or non-anonymized partial/full collections can be transferred to research entities after release by participant. Pathological collections from multiple participants can be researched as part of a study by the research entity only.

Figure 4:
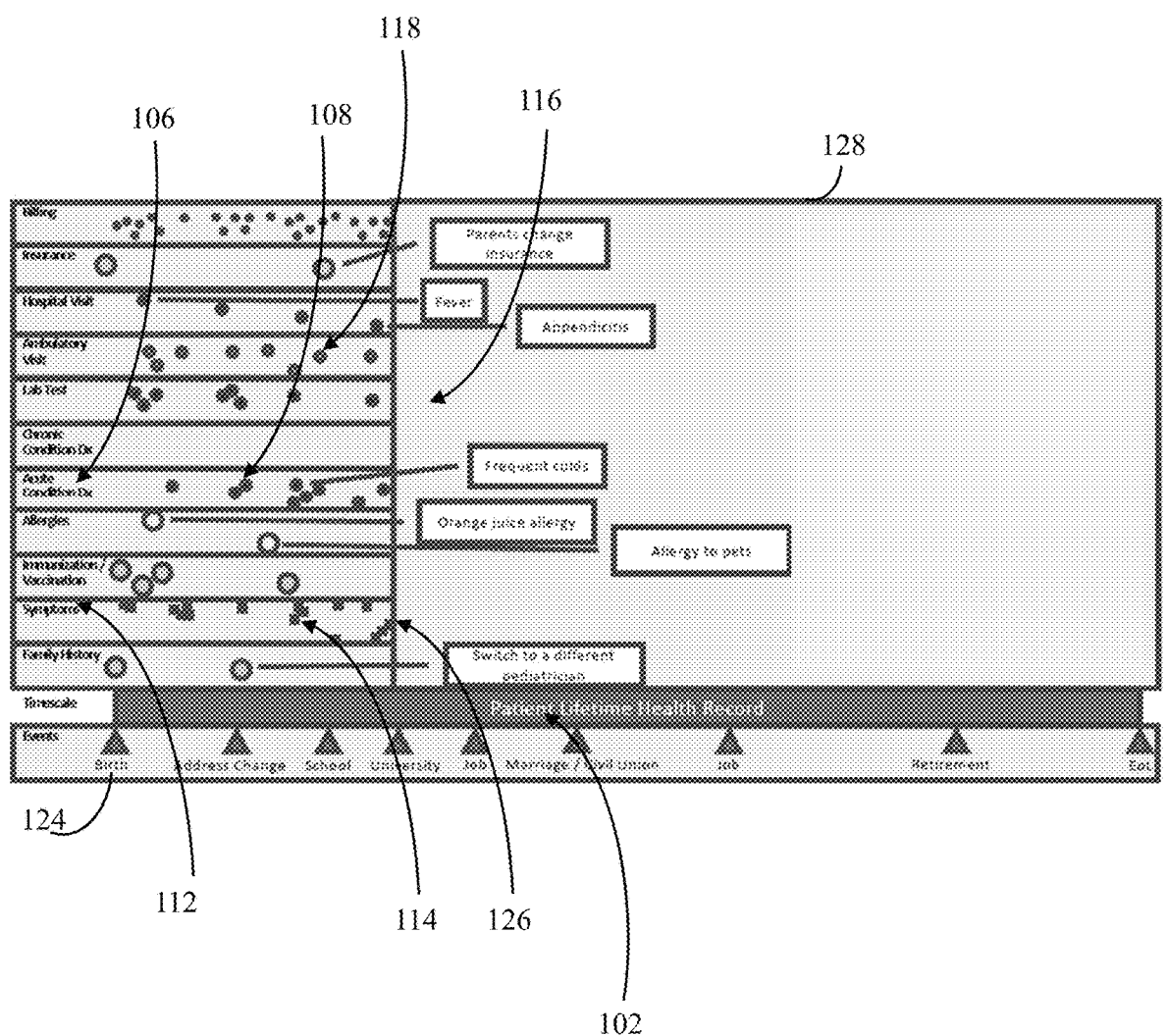
FIG. 4 is an illustration of participant data collected by a parent.

FIG. 4 depicts an additional embodiment of the system 100 wherein a first participant 102 inputs data into the system 100, wherein the symptom data 112 and resulting encrypted symptom event blocks 114 generated therefrom are collected by the first participant 102 using at least one symptom collection device 110 to assess, quantify and record the symptoms belonging to a second participant 102 on behalf of the second participant 102. In this instance the first participant 102 may also function as a gatekeeper 124 to manage access to data representing a digital health record of the second participant 102. FIG. 4 depicts decentralized ledger blocks 118 comprising event data corresponding to both diagnosis data 106 representing and contained within encrypted diagnosis event blocks 108, and symptom data 112 representing and contained within encrypted symptom event blocks 114, wherein the depicted events represent the same specific categories of structured data as depicted in FIGS. 2-3. In the additional embodiment depicted by FIG. 4 a first participant 102 who also functions as a gatekeeper 124 begins collecting event data including symptom data 112 at the birth of a second participant 102, where the first participant 102 may be a parent or legal guardian of the second participant 102 entrusted to manage health data on behalf of the child second participant 102. Relevant data may be displayed to the first participant 102 using an interface 128 that in response to action directives 132 displays pathology collections 126 processed using the network 120 of secure processing devices 122 on the interface 128, which then allows the first participant 102 to share access to portions of the secure chain 116 of decentralized ledger blocks 118 and pathology collections 126 with other authorized participants 102 including physicians or other health care professionals. Pathology collections 126 are stored for participant 102 use with the interfaces 128 and applications of the system 100 by retrieving data from the digital health record stored in the secure chain 116 of decentralized ledger blocks 118 residing in the network 120 of secure processing devices 122 functioning as an encrypted data farm. Each participant 102 can share this data with other participants 102 including healthcare providers and payers. Complete digital health records (DHRs) can lead to more accurate and timely diagnosis. Each participant 102 can join one or more research projects, including various types of studies, and release temporarily, partial or full DHR in an anonymized or non-anonymized format with the requesting participant 102 comprising the particular research entity. Pathology collections 126 from multiple participants 102 can be researched as part of a study by the research entity only based on security and restrictions set by the network 120, administrator of the network 120, and gatekeepers 124. The event data in FIG. 4 comprises events from the birth at a hospital of the second participant 102 until graduation from high school creating a comprehensive and integrated digital health record, that includes family histories taken at birth and at the time of the family move to a different city, receiving recommended vaccinations at birth, hospital visits related to fever, appendectomy, data indicating frequent colds, ambulatory care at a pediatrician for, no chronic conditions, subsequent developments of multiple allergies, a set of multiple symptoms, primarily related to colds, continuous coverage on her parents insurance and lab tests performed around most visits. The structured data and links between event data represented in the secure chain 116 of decentralized ledger blocks 118 preserve the sequence, timing, and interrelation of events using time stamps and structured data embedded in the blocks.

Figure 5:
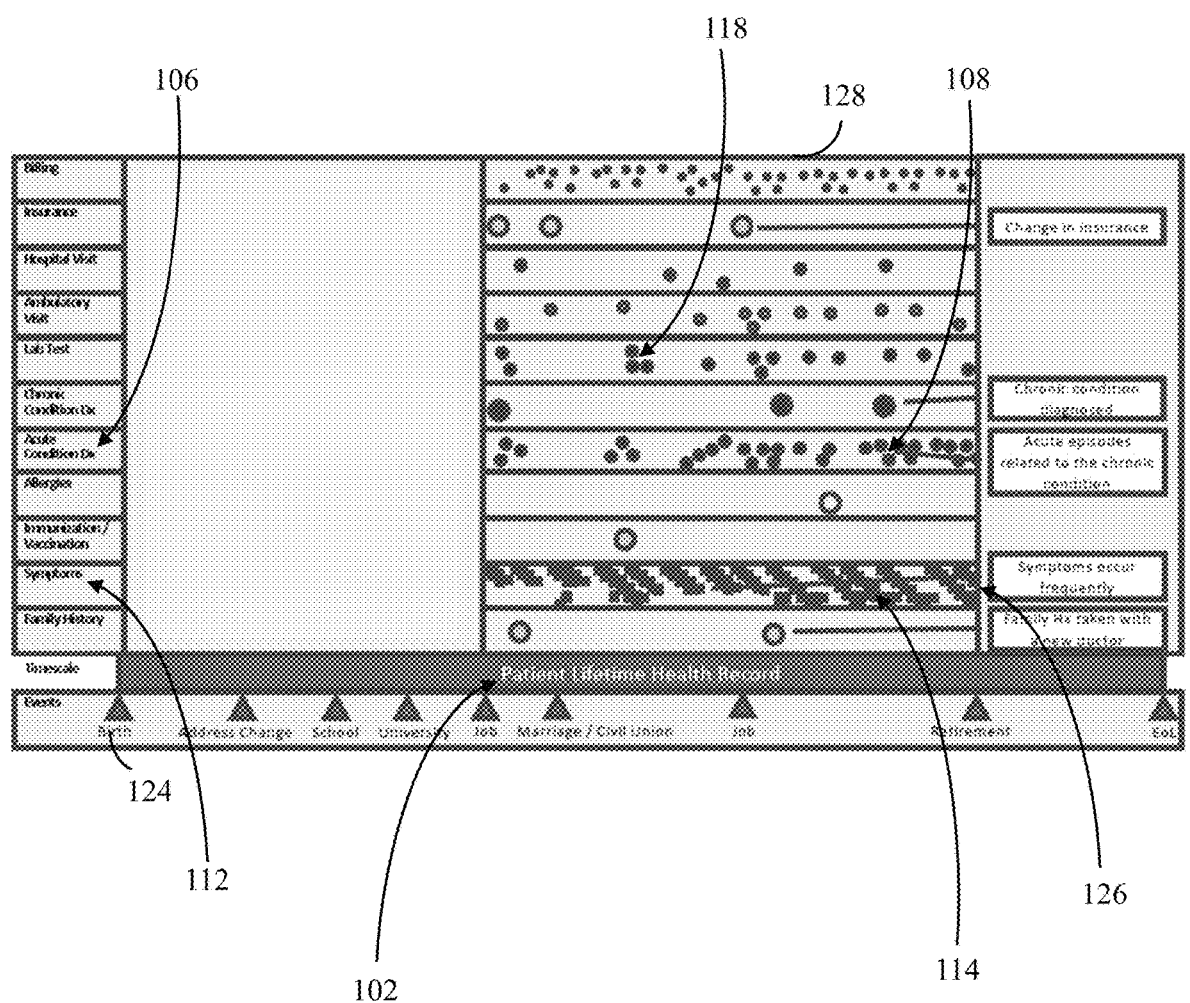
FIG. 5 is an illustration of participant data collected by the participant.

FIG. 5 depicts an illustrative embodiment of the system 100 wherein an interface 128 displays decentralized ledger blocks 118 comprising event data corresponding to both diagnosis data 106 stored within encrypted diagnosis event blocks 108, and symptom data 112 stored within encrypted symptom event blocks 114, corresponding to a digital health record displaying the same specific categories of structured data as depicted in FIGS. 2-4. FIG. 5, however, depicts an embodiment wherein a participant 102 subscribes to participate during the participant's 102 lifetime and uses a symptom collecting device 110 to enter that participant's 102 own symptom data 112, generating encrypted symptom event blocks 114 therefrom. The collection of data begins when the participant 102 signs up for the application, accepting the terms of use, and begins entering participant 102 health data. Adult participant 102 enters their data until retirement. The participant 102, using the application together with an interface 128, tracks their symptoms in real time, longitudinally, with all the necessary details, and links them at a later time to a diagnosis provided by the physician. The participant 102 also uses the application and system 100 to engage in management of multiple doctors including communication between multiple health care systems. The interface 128 displays that at the time participant 102 subscribes, the participant 102 fills out information about past medical history has one problem or chronic condition, and then acquires two more problems and chronic conditions. The interface 128 also displays the participant 102 changes insurance at several life changing events, and due to problems and chronic conditions, frequently utilizes ambulatory care, and may have frequent acute episodes. Continuity of care and detailed documentation of acute episodes, symptoms, and medication being taken is highly important, and it is successfully recorded and analyzed using the secure chain 116 of decentralized ledger blocks 118 of the system 100.

Figure 6:
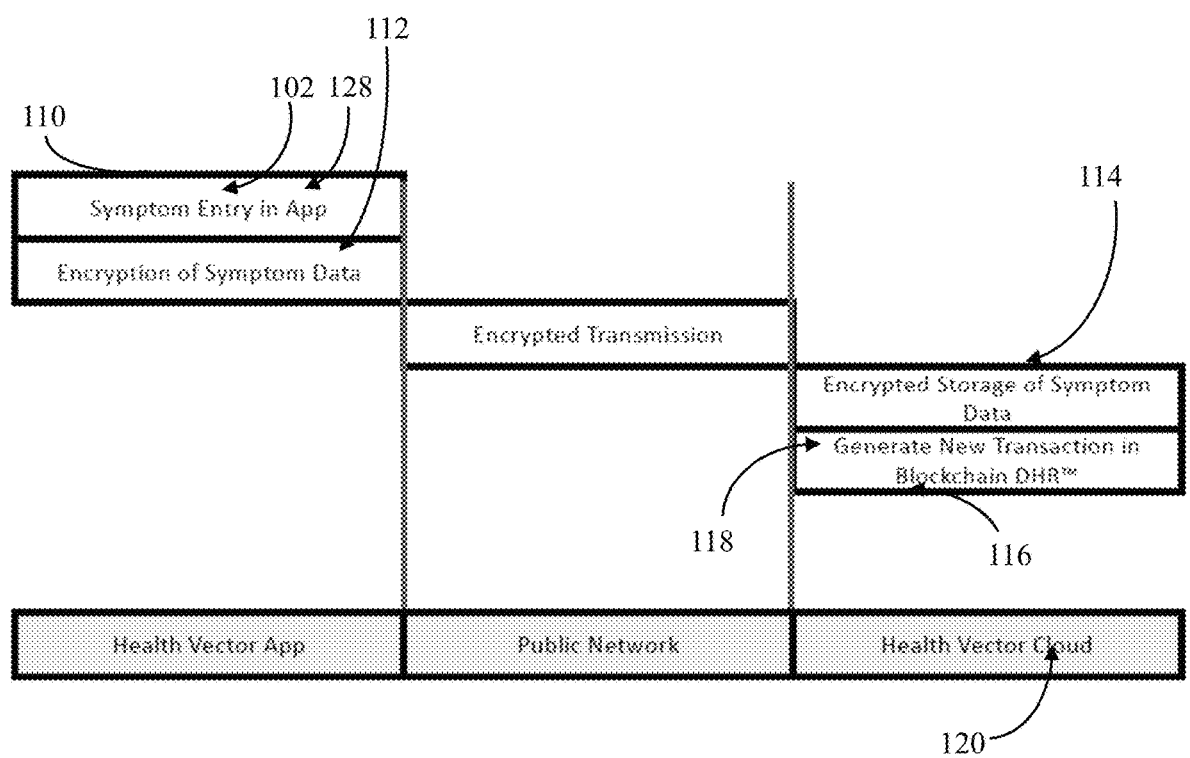
FIG. 6 is an illustration of system symptom acquisition and encryption.

FIG. 6 depicts an illustrative embodiment of the system 100 wherein a participant 102 uses a symptom collecting device 110 to record and store symptom data 112 in the system 100 by entering the symptom data 112 using an application downloaded into and stored in the symptom collecting device 110. The symptom data 112 may be entered as structured data, unstructured data, or unstructured data that is converted to structured data by the application by using resources provided by the secure network 120 of secure processing devices 122. Upon entry of symptom data 112, the application performs encryption of the symptom data 112. The encrypted symptom data 112 is then sent using the application and wired or wireless data protocols over public networks as an encrypted transmission to the secure network 120 of secure processing devices 122. The secure processing devices 122 of the network 120 generate different decentralized ledger blocks 118 in a subset of the secure processing devices 122 and import data from the existing secure chain 116 of decentralized ledger blocks 118 to appropriately link the newly generated blocks to the secure chain 116. The encrypted symptom data 112 is recorded in each of the newly generated blocks to generate encrypted symptom event blocks 114 thereby constructing the newest linked blocks in the secure chain 116 of decentralized ledger blocks 118 stored using secure processing devices 122 of the network 120. In other embodiments the network 120 of secure processing devices 122 may function as a cloud computing environment with encryption and protocols to preserve privacy and security of all data present within the network 120. Once the symptom data 112 is successfully stored as encrypted symptom event blocks 114 in the secure chain 116, the system 100 can aggregate and integrate the data to perform various analyses and action directives 132, including the formation of pathology collections 126 and reports 130 that allow participants 102 to review the data uniquely integrated so as to gain insight into patterns of symptoms, diagnoses, treatments and other data in real time that would not be possible using conventional health data systems.

In other embodiments of the present invention, the integrated longitudinal condition tracking system 100 can include a symptom collecting device 110 comprising one or more of the group consisting of an imaging device, a recording device, self-administered diagnostic instruments and an authorized participant 102 computing device configured to receive and store symptom data 112 input by a participant 102. A symptom collecting device 110 can digitize symptom data 112 and upload the symptom data 112 to the network 120 of secure processing devices 122. A participant 102 may also enter the data manually via notes with structured data fields and free text describing various aspects of their symptoms. These aspects may include details about when the symptom started, its progression, accompanying details, aggravating factors, alleviating factors, and other information the participant 102 may wish to include. Additionally, a participant 102 can document their symptoms by recording or uploading pictures, video and audio of the affected areas of their body. The participant 102 can supplement the free text symptom note by uploading digitized documents (e.g., photos, scanned files, emails, etc.). All the data are encrypted at the device and then sent, encrypted, to a database, cloud or decentralized ledger blocks 118 of the network 120 where they are stored and encrypted, as well. In another embodiment, a participant 102 may also enter symptoms using a click-&-speak function for quick entry using the voice recognition functions of a symptom collecting device 110 that may be configured as a type of mobile device. Once entered, the symptom name is verified against a database of existing symptoms stored in the network 120 and then the symptom name is entered in the structured data field for symptoms and in long text stored in the system 100. In another embodiment, a participant 102 may also enter symptoms using the quick entry by typing or saying the symptom and a dropdown menu allows the participant 102 to select a symptom from the database. If the symptom cannot be found, then the symptom is entered by the participant 102 as free text and is saved as is. In another embodiment, a participant 102 may also enter symptoms using the detailed entry by typing or saying the symptom or a drop-down menu allowing the participant 102 to select the symptom(s) from the database. If a desired symptom cannot be found in the database, the symptom entered by the participant 102 as free text is saved as is. The participant 102 can enter additional details regarding the symptoms and signs by responding to a set of standardized questions addressing the progression, the aggravating factors, the alleviating factors, location and activities the participant 102 was performing while feeling the symptoms. In another embodiment, a device, including a diagnosis acquisition device 104 or a symptom collection device 110, can monitor and report a symptom automatically into the application or network 120 of the system 100.

Figure 7:
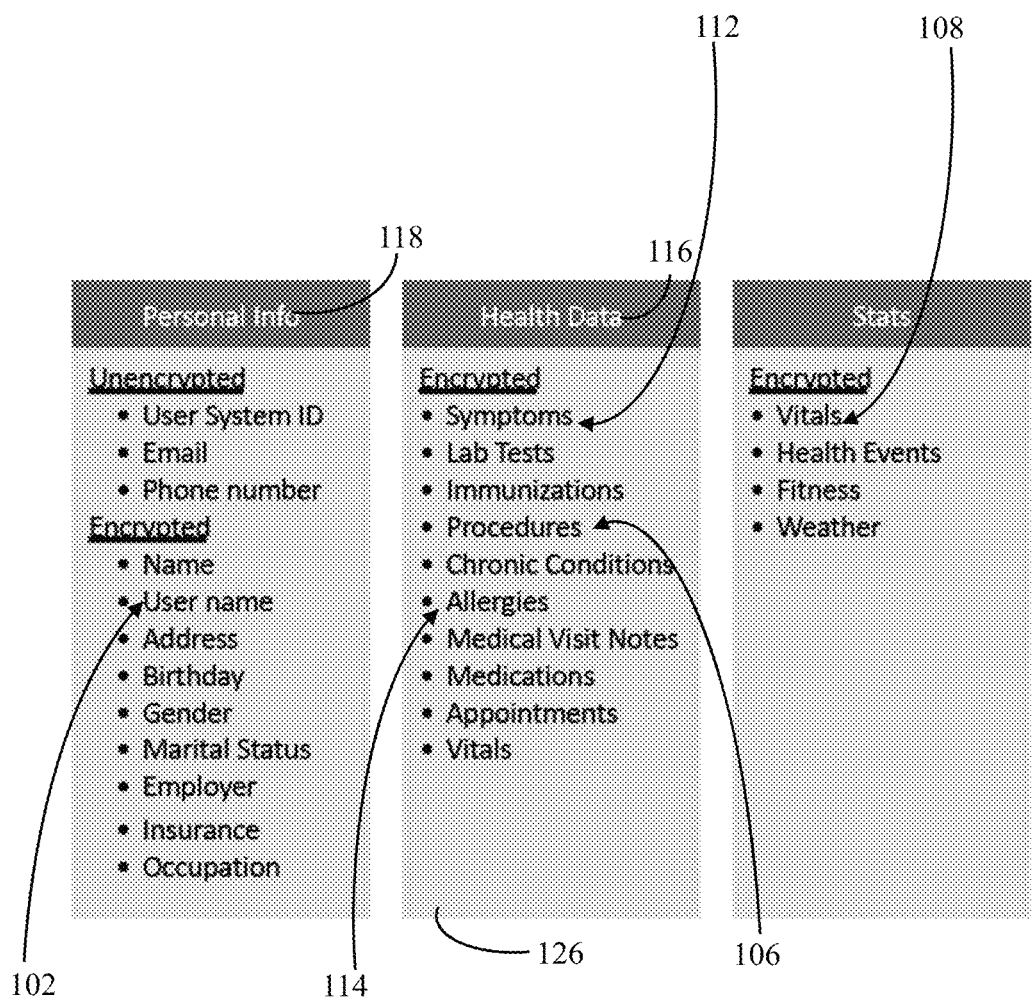
FIG. 7 is a diagram of encryption standards applied to data subsets.

To preserve the privacy and security of data related to participants 102 the system 100 provides multiple layers of data encryption. FIG. 7 depicts an illustrative embodiment of the system 100 wherein advanced encryption standards are applied to specific sets of data entered, processed, or stored in the system 100, based on rules and criteria stored within the secure processing devices 122 of the network. A limited set of specific person information is left unencrypted due to its function as contact information. Such personal information may include User/participant system ID, email address, and phone number belonging to the participant 102. Personal information, health data and statistics stored in the system 100 may be encrypted using advanced encryption standards AES 128, 192 or 256. Personal information encrypted pursuant to these standards may include name, user name, address, birthday/birthdate, gender, marital status, employer, insurance data, occupation data or other personally identifiable information. Health data encrypted pursuant to these standards to be recorded as encrypted symptom event blocks 114 or encrypted diagnosis event blocks 108 may include symptoms, lab tests, immunizations or vaccinations, procedures, problems and chronic conditions, acute conditions, allergies, medical visit notes, medications prescribed or administered, appointments scheduled or completed, vitals, or other commonly known health data related to a participant 102. Statistics processed and analyzed by the system 100 that may be encrypted pursuant to these standards may include vitals, health events, fitness, weather, or other information useful to associate with one or more participants 102. More specifically, the structured data in the system 100 that may be encrypted and stored in the secure chain 116 of decentralized ledger blocks 118 can comprise one or more of the group consisting of symptom name data, additional accompanying symptom data 112, date and time data, participant 102 note data, problem and chronic condition links, alleviating factor data, aggravating factor data, frequency data, duration data, perception data, description data, trend data, environmental factor data, weather data and history data. Encryption of data can be performed using Advanced Encryption Standard (AES) 11 128, 192, or 256-bit encryption.

To further improve data privacy and security, each symptom, diagnosis or other participant 102 event is recorded in a transaction on a private blockchain ledger. The recording of the symptom data 112 is immutable and not vulnerable to change of any details of the records stored on the ledger due to the nature of the decentralized ledger. Each symptom record can include structured data, the main symptom name, additional accompanying symptoms, date and time, location, long text, problem and chronic condition link, alleviating and aggravating factors, frequency, duration, perception/description, trend, activity, weather conditions, and/or environmental factors. This data is encrypted into a block entry in the private blockchain ledger that forms the secure chain 116 of decentralized ledger blocks 118 stored in the system 100. The symptom data 112 may be stored as part of a digital health record owned by a participant 102. Digital health records and digital medical records are based on block chain technology that makes it extremely difficult to modify records and data already stored on the block chain. A private key or public key is required to access a particular block or block chain data. The private key is unique to each block chain and is needed to generate a new transaction on the block. If symptom data 112, diagnosis data 106, other event data, system 100 and/or other medical record data or health data are stored in the block chain of the secure chain 116 of decentralized ledger blocks 118, the private key belonging to the participant 102 would be needed to modify the records. Each entry in a block chain relates to one event or note, so all health information is distributed and encrypted, therefore proving to be safe and difficult to compromise. In another embodiment of the present invention, the integrated longitudinal condition tracking system 100 can comprise encrypted diagnosis event blocks 108 and encrypted symptom event blocks 114 that are encrypted with a private key unique to each secure chain 116 and possessed by to the gatekeeper 124 that is a component of a public key-private key infrastructure, wherein modification may only be accomplished through access granted by the private key.

Figure 8:
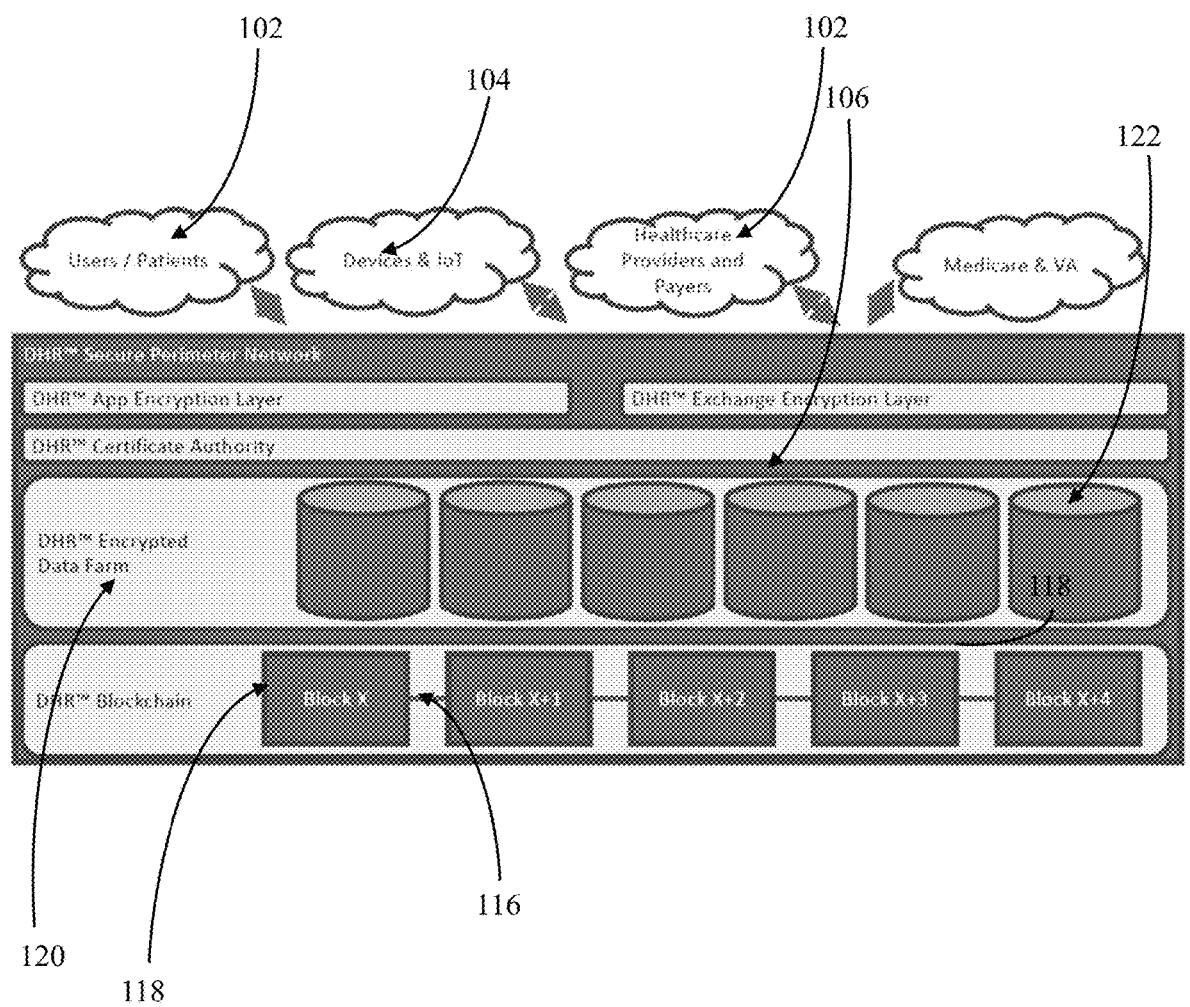
FIG. 8 is an illustration of functional encryption layers.

FIG. 8 depicts an illustrative embodiment of the system 100 wherein a variety of different participants 102 and devices interact with the system 100 and data therein that are all secured using multiple layers of encryption protection. Participants 102 include patients and/or users, various healthcare providers and/or payers, benefits and social welfare organizations including those related to Medicare programs and veterans affairs. Devices include diagnosis acquisition devices 104 and symptom collecting devices 110 as well as other healthcare devices and internet-of-things devices. Each participant 102 or device, communicating with the system 100 using wired or wireless communication protocols, must present valid subscription credentials subject to verification by the system 100 in order to access the secure network 120 of secure processing devices 122 maintained by the system. Data of the system is further protected by an application encryption layer, an exchange encryption layer, encryption applied to the components of the network 120 of secure processing devices 122 functioning to create an encrypted data farm, and the discussed encryption and security features of block chains possessed by the secure chain 116 of decentralized ledger blocks 118. The network 120 uses full disk encryption (FDE) signifying that everything on disk is encrypted. Disk encryption uses disk encryption software or hardware to encrypt every bit of data that goes on a disk or disk volume. It is used to prevent unauthorized access to data storage and secure the perimeter of the system. Layers of encryption further include a Blockchain layer comprising a permissioned private blockchain, and additionally, can be augmented by linking to a semi-decentralized consortium blockchain. An Additionally Encrypted layer may comprise a secure data farm using Amazon AWS or Microsoft Azure data encryption standards for HIPAA implementations. DHR Certificate Authority can comprise using Amazon AWS or Microsoft Azure certificate authority to provide secure access to data. DHR Exchange Encryption Layer comprises data exchange encryption standard AES—Advanced Encryption Standard (AES) 11 128, 192, or 256-bit encryption; and a DHR Application Encryption Layer can comprise data exchange encryption standard AES—Advanced Encryption Standard (AES) 11 128, 192, or 256-bit encryption.

In addition to allowing participants 102 private and secure access to data stored in the secure chain 116 for analysis and review, the system 100 can maintain privacy and security while interacting with external networks and resources, for example by integrating the structured participant 102 symptom data 112 and other data stored in the network 120 of secure processing devices 122 in order to schedule a medical appointment with an external entity. During appointment set up, the participant 102 links the related symptom data 112 to the appointment using action directives 132. The participant 102 connects or electronically communicates with patient portals and uploads the symptom data 112 into the electronic medical records and/or electronic health records maintained by the entity associated with the appointment. The data integration dramatically improves physician-patient relationships, health data management technology and overall quality of care by providing symptom data 112 to healthcare providers in a timely and structured presentation. Once scheduled, the appointment information is communicated back into the system 100 and stored into a new entry in the secure chain 116 of decentralized ledger blocks 118 with all relevant data encrypted. This block can be accessed by the participant 102 via a private key and by the healthcare provider with the appropriate credentials approved by the gatekeeper 124. The participant 102 may further trigger the electronic transmission of the appointment relevant data to the electronic medical records and/or electronic health records used by the healthcare provider. In an another embodiment of the integrated longitudinal condition tracking system 100, one or more stored action directives 132 may automatically create an appointment generated and scheduled from data derived from the pathology collections 126 linking encrypted symptom event blocks 114 to appointment attributes set by a participant 102, and wherein once set, the action directive 132 generates an encrypted diagnosis event block 108. In this way patterns identified with risks to participants 102 can be discovered by the system 100 in a timely fashion and medical assistance can be scheduled without the delays associated with communicating symptoms to medical professionals, inquiries related to scheduling appointments with healthcare providers or pre-appointment activities related record maintenance or verification of symptoms or medical history.

Figure 9:
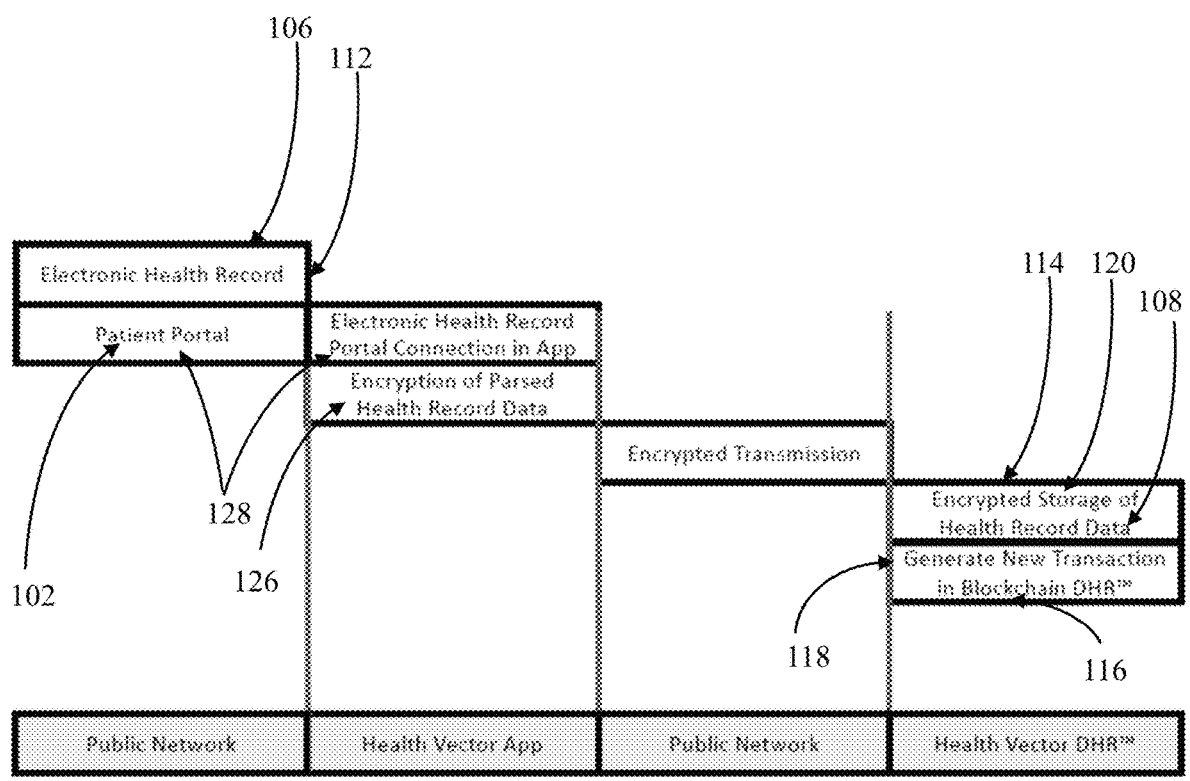
FIG. 9 is an illustration of integrated symptom acquisition and encryption.
Figure 10:
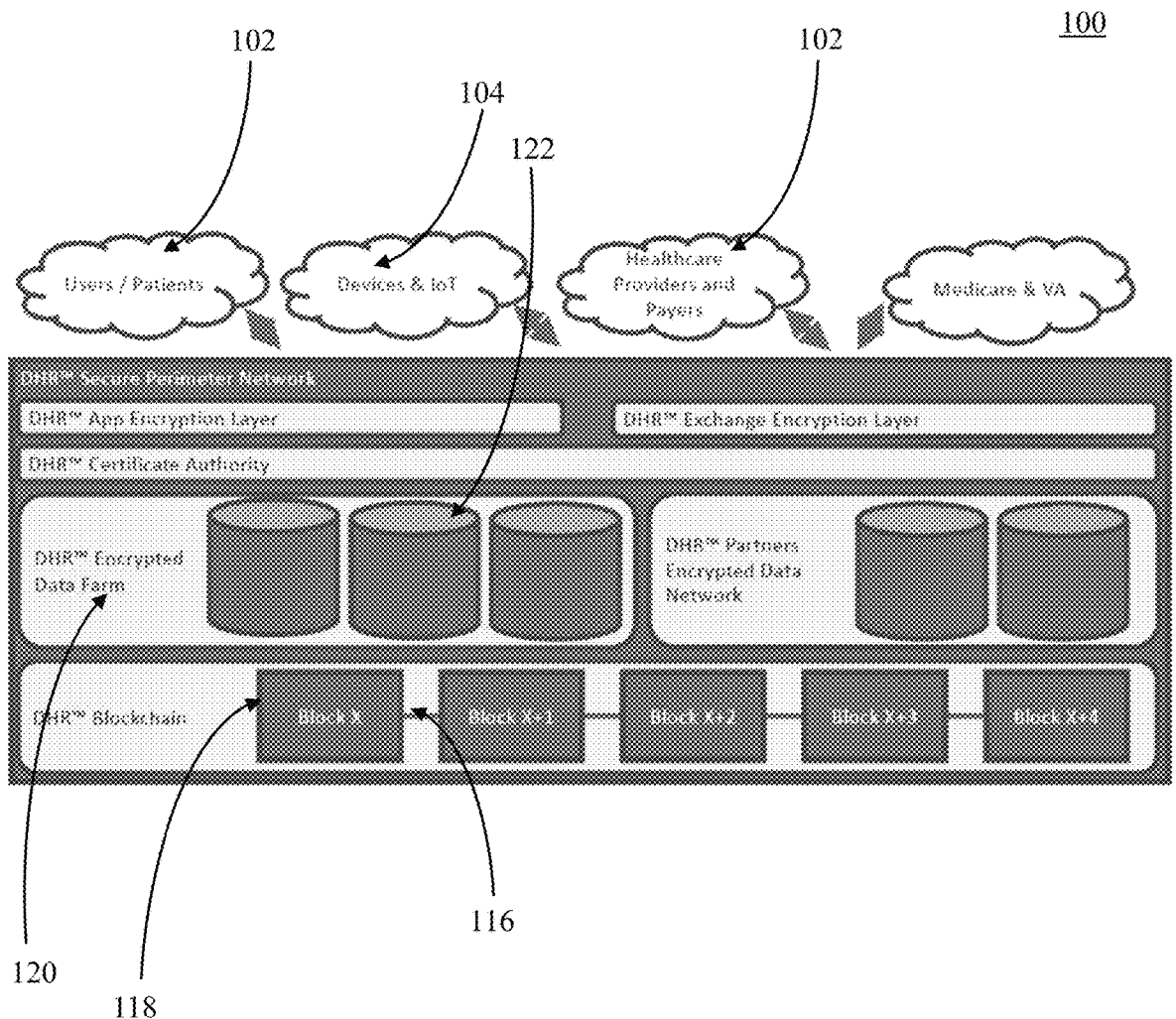
FIG. 10 is an illustration of integrated functional encryption layers.

FIGS. 9-10 depict other embodiments of the present invention related to FIGS. 6 and 8, respectively; however FIGS. 9-10 are the product of the discussed integration of data. In FIG. 9, after the system 100 transmits symptom data 112 related to an appointment, or otherwise engages with an external network associated with a participant 102, and the system 100 communicates with the external network, which may be by use of a patient portal for a participant 102 who is a patient of a participating health care provider. The system 100 retrieves the electronic health record data and stores that data in the system 100 where it may then make that data available to a participant 102 using an application to review the data. The electronic health record data may be entered as structured data, unstructured data, or unstructured data that is converted to structured data by the application by using resources provided by the secure network 120 of secure processing devices 122. Upon entry of electronic health record, the application and system 100 perform encryption of the electronic health record data. The encrypted data is then sent using the application and wired or wireless data protocols over public networks as an encrypted transmission to the secure network 120 of secure processing devices 122. The secure processing devices 122 of the network 120 generate different decentralized ledger blocks 118 in a subset of the secure processing devices 122 and import data from the existing secure chain 116 of decentralized ledger blocks 118 to appropriately link the newly generated blocks to the secure chain 116. The encrypted symptom data 112 is recorded in each of the newly generated blocks as described with respect to FIG. 6. Additionally, FIG. 10 differs from FIG. 8 where the variety of different participants 102 and devices interact with the system 100 and data therein include partner encrypted data networks that as demonstrated by FIG. 9, add steps to interactions but also supply additional encryption.

In another embodiment of the present invention the system 100 performs functions to enable the participant 102 to integrate symptoms and medical information into a digital health record or digital medical record kept by another participant 102 such as health care professional entities. The participant 102 can access participant's 102 own data in the secure chain 116 of decentralized ledger blocks 118 as part of the digital health record. When a participant 102 accesses their patient portal and downloads the electronic health record into the system 100 application, the information is parsed according to the Fast Healthcare Interoperability Resources standard and the proprietary system 100 data architecture in the cloud comprising the network 120 of secure processing devices 122. The individual health record components are encrypted and stored into the private blockchain ledger of the secure chain 116 of decentralized ledger blocks 118 as part of the participant's 102 digital health record. This measure ensures the privacy and safety of the data. The ledger components may be the following: medications, immunizations, lab test, procedure, chronic, allergies, medical visit, appointments. Components can be linked together in the network 120 based on related events and conditions. The consolidated blockchain for each participant 102 results in the comprehensive health record including the symptoms in a structured data format. When the participant 102 grants the healthcare providers access to their data through the system 100 application or EMR/EHR interface 128, the provider, as an authorized participant 102, can create or modify the relationships between symptoms, diagnosis, medications, conditions and other components. The relationship can be defined during or after the medical visit. Each interaction is logged, traced and stored as part of the transactions performed on the digital health record. Each transaction is stored in the secure chain 116 of decentralized ledger blocks 118. Both the patient and the physician participants 102 can link symptom data 112 to diagnosis data 106, assessment and treatment plan, and track over time the symptom data 112 related to certain diagnosis data 106 and treatment plan. All the data are fully encrypted and available to the participant 102 and, if shared, the healthcare provider. The integrated longitudinal condition tracking system 100 can be configured to use the network 120 of secure processing devices 122 to add additional data, structured data, and limit access to the secure chain 116 based on privacy restrictions and security restrictions input into the network 120 of secure processing devices 122 by authorized participants 102 that may include the gatekeeper 124. The privacy settings allow the gatekeeper 124 to select the fields in the symptom note, or the supplemental documents, to be shared with the healthcare provider. Only the gatekeeper-selected notes and symptom data 112 are included. Through the use of OCR translation technology, the printed documents scanned by the participant 102 may be parsed and included into the digital health record. To be available to the healthcare provider, the data can be transmitted electronically directly either to the electronic health record or provided as PDF file. Similar process applies to sharing the symptom notes or other digital health record data with the participant's 102 insurance company or payer. The interface 128 can be further configured to allow the participant 102 to review the decentralized ledger blocks 118 in a set over an input time period and add links further integrating the decentralized ledger blocks 118, and the interface 128 can be further configured to allow the participant 102 to share pathology collections, decentralized ledger blocks 118 and structured data thereof with another participant 102. The interface 128 can also be configured to allow the participant 102 to view pathology collections, decentralized ledger blocks 118 and structured data thereof for an aggregation of anonymized participants 102, wherein aggregation and anonymization are controlled by structured data in the secure chain 116. A HIPAA compliant cloud is used to store data, for example Amazon AWS or Microsoft Azure clouds. Additionally all transmissions from other sources are encrypted with the AES encryption standard.

In another embodiment of the present invention, the integrated longitudinal condition tracking system 100 can further comprise an interface 128 wherein the participant 102 can enter data into network 120 of secure processing devices 122 to create pathology collections 126 that are configured based on input from a participant 102, thereby integrating diagnosis data and symptom data 112 according to data entered by the participant 102.

In another embodiment of the present invention, the interface 128 can be further configured to allow the participant 102 to review the decentralized ledger blocks 118 in a set over an input time period and add links further integrating the decentralized ledger blocks 118, and the interface 128 can be further configured to allow the participant 102 to share pathology collections, decentralized ledger blocks 118 and structured data thereof with another participant 102. The interface 128 can also be configured to allow the participant 102 to view pathology collections, decentralized ledger blocks 118 and structured data thereof for an aggregation of anonymized participant 102s 102, wherein aggregation and anonymization are controlled by structured data in the secure chain 116.

In another embodiment of the present invention, the interface 128 can be further configured to allow the participant 102 to review the decentralized ledger blocks 118 in a set over an input time period and add links further integrating the decentralized ledger blocks 118, and the interface 128 can be further configured to allow the participant 102 to share pathological collections, decentralized ledger blocks 118 and structured data thereof with another participant 102. The interface 128 can also be configured to allow the participant 102 to view pathological collections, decentralized ledger blocks 118 and structured data thereof for an aggregation of anonymized participants 102, wherein aggregation and anonymization are controlled by structured data in the secure chain 116.

Figure 11:
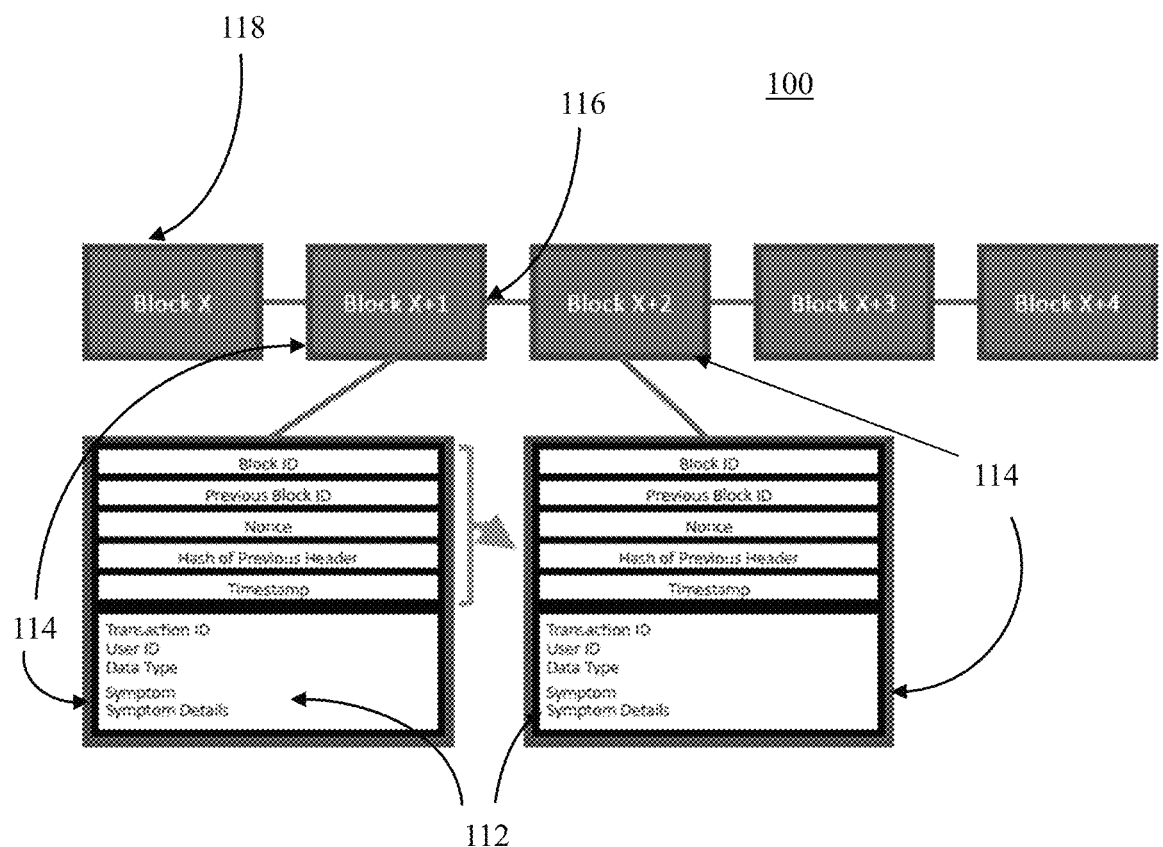
FIG. 11 is a diagram of symptom data stored in a Blockchain block.
Figure 12:
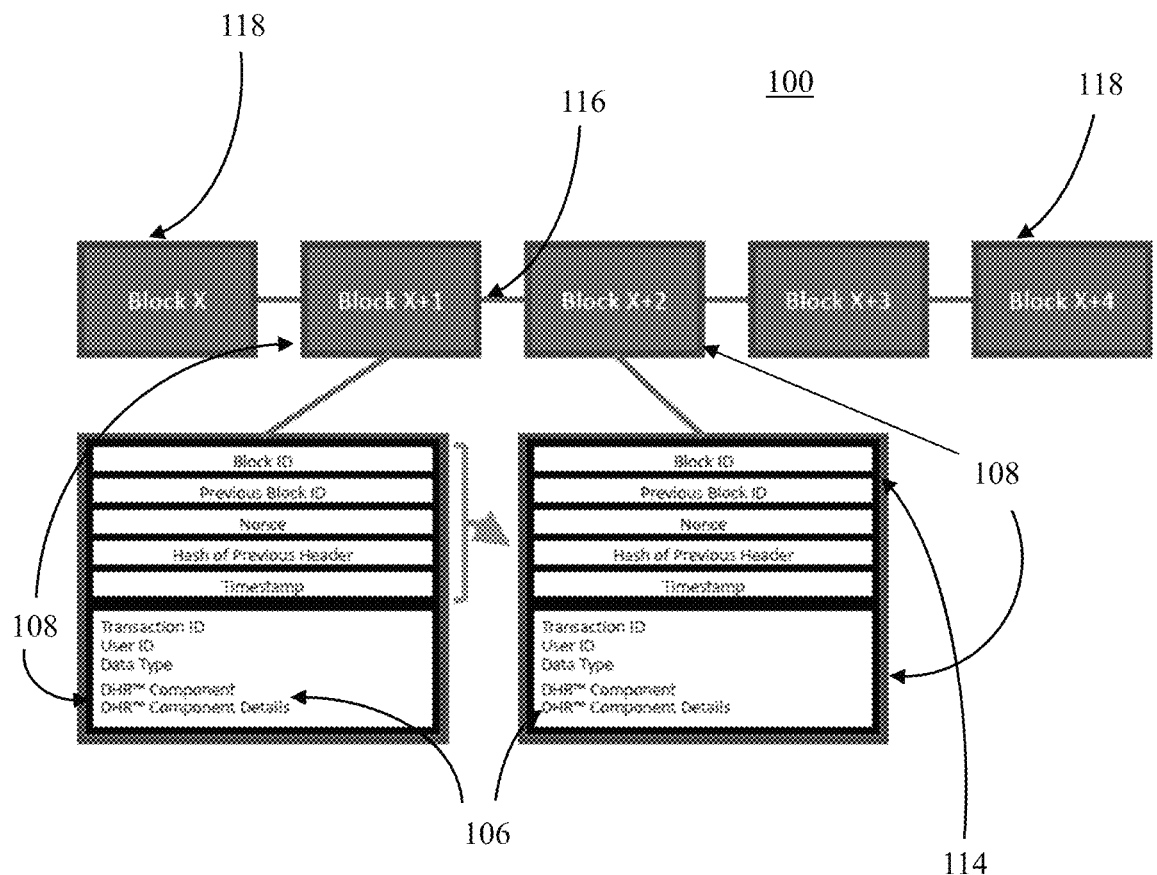
FIG. 12 is a diagram of component data stored in a Blockchain block.

FIG. 11 depicts an exemplary embodiment comprising a chain of five successive linked blocks forming a subset of the secure chain 116 of decentralized ledger blocks 118, identified for reference as Block X, Block X+1, Block X+2, Block X+3 and Block X+4. These blocks record and store symptom data 112 and are thus encrypted symptom event blocks 114 of the system 100. FIG. 11 further depicts the data stored within, and interrelation of, Block X+1 and Block X+2. Block X+1 comprises structured data fields for Block ID, Previous Block ID, Nonce, Transaction ID, User ID, Data Type, Symptom and Symptom Details. Block X+2 similarly comprises structured data fields for Block ID, Previous Block ID, Nonce, Transaction ID, User ID, Data Type, Symptom, Symptom Details. In accordance with aspects of the present invention, each of the decentralized ledger blocks 118 in the secure chain 116 of decentralized ledger blocks 118 comprises a hash of a previous block in the secure chain 116 and hashes related to links to other blocks derived from structured data associated with the decentralized ledger blocks 118. FIG. 12 depicts an additional embodiment of the present invention wherein Block X+1 and Block X+2, in addition to storing Block ID, Previous Block ID, Nonce, Transaction ID, User ID, and Data Type as in FIG. 11, instead store a digital health record component, digital health record component details, generalizing the type of data that may be captured and stored within decentralized ledger blocks 118 of the secure chain 116, including diagnosis data 106 and diagnosis details, in which case those blocks are encrypted diagnosis event blocks 108.

Figure 13:
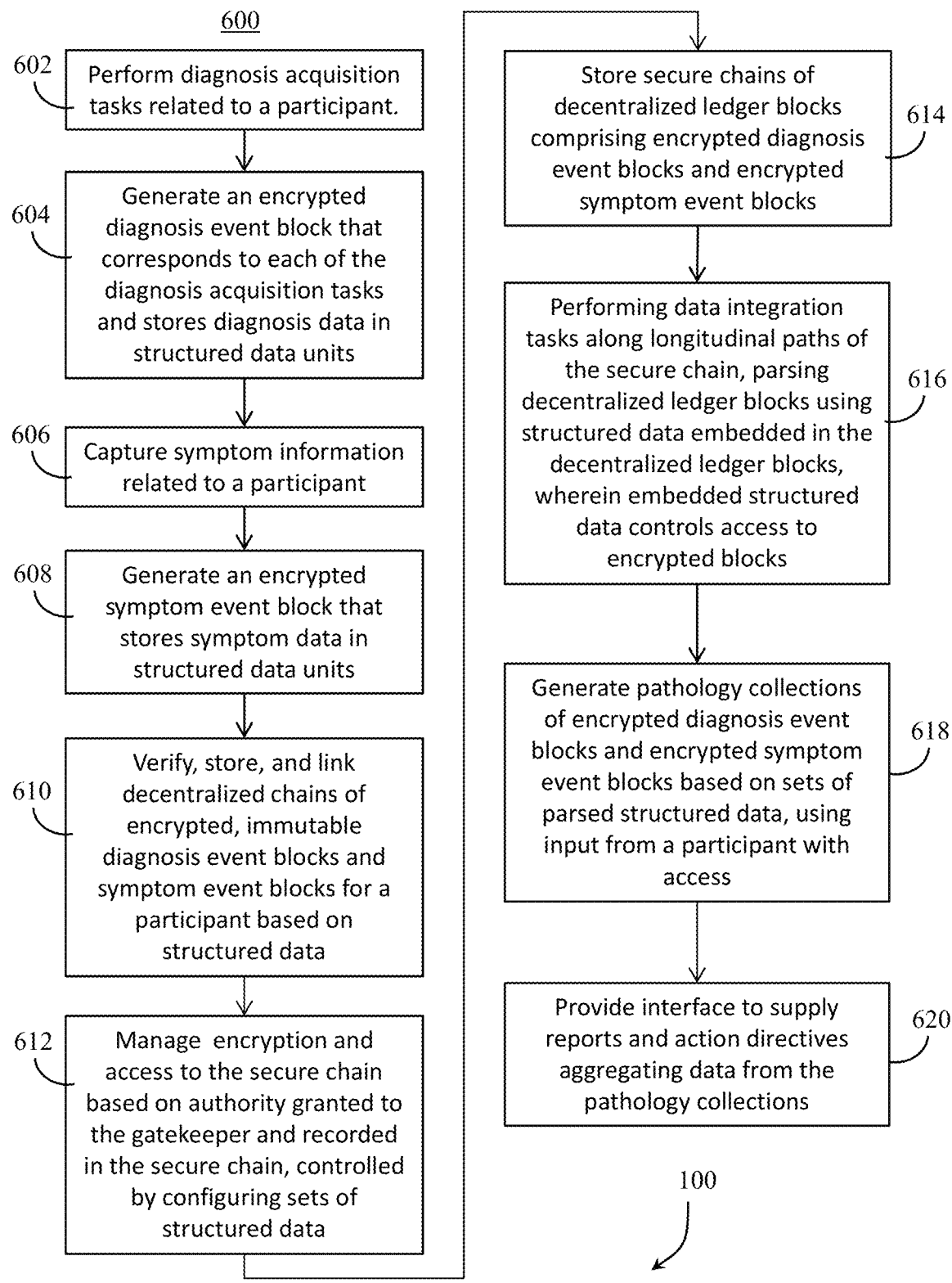
FIG. 13 is an illustrative flowchart showing an example embodiment of a method for performing one or more functions of the embodiments of the present invention.

FIG. 13 depicts an exemplary flowchart showing an example embodiment of a method 600 for carrying out operation of the system 100 of the present invention to provide integrated longitudinal condition tracking. At step 602, at least one diagnostic acquisition device 104 performs diagnostic acquisition tasks related to a participant 102 and generates at step 604, using the diagnostic acquisition device 104, an encrypted diagnosis event block 108 that corresponds to each of the diagnosis acquisition tasks performed and stores diagnosis data 106 in structured data units therein. At step 606, a symptom collecting device 110 captures symptom information related to a participant 102 and generates at step 608, using the symptom collecting device 110, an encrypted symptom event block 114 that stores symptom data 112 in structured data units therein. At step 610 the method uses a secure chain 116 of decentralized ledger blocks 118 to verify, store, and link decentralized chains of encrypted diagnosis event blocks 108 and encrypted symptom event blocks 114 for a participant 102 based on the structured data, which renders the encrypted diagnosis event blocks 108 and encrypted symptom event blocks 114 of the secure chain 116 immutable and secure. At step 612 a gatekeeper 124 may be used to manage encryption and access to the secure chain 116 based on authority granted to the gatekeeper 124 and recorded within the secure chain 116. The gatekeeper 124 possesses authority to grant and deny access to subsets of the secure chain 116 by one or more participants 102, wherein access is controlled by configuring sets of structured data. At step 614, a network 120 of secure processing devices 122 stores each of the secure chains 116 of decentralized ledger blocks 118 comprising encrypted diagnosis event blocks 108 and encrypted symptom event blocks 114 received from participants 102 via diagnostic acquisition devices and diagnosis acquisition devices 110. At step 616, the method uses the network 120 of secure processing devices 122, together with a set of historic instructions stored in the system 100 and/or input from one or more participants 102, to perform data integration tasks, wherein the network 120 of secure processing devices 122 processes data, migrates along longitudinal paths of the secure chain 116, and parses decentralized ledger blocks 118 using structured data embedded in the decentralized ledger blocks 118. The structured data embedded in the decentralized ledger blocks 118 controls access to encrypted diagnosis event blocks 108 and encrypted symptom event blocks 114 based on access granted by the gatekeeper 124. At step 618, the method uses a portion of the network 120 of secure processing devices 122 together with decentralized ledger blocks 118 contained therein, and generates pathology collections 126 of encrypted diagnosis event blocks 108 and encrypted symptom event blocks 114 based on sets of parsed structured data. The pathology collections 126 may be configured based on input from a participant 102, subject to access granted to the participant 102 by the gatekeeper 124, wherein a properly authorized participant 102 may access stored pathology collections 126 by inputting particular terms via at least one of the interfaces 128 of the system 100, or may create new pathology collections 126 by using the interface 128 to input a set of terms corresponding to structured data, creating and using various action directives 132, that are then used to access and aggregate related decentralized ledger blocks 118 and data therein from the secure chain 116 of decentralized ledger blocks 118 for relevant participants 102 and health records thereof stored in the network 120 of secure processing devices 122. At step 620, the method uses at least one interface 128 provided as part of the system 100 to supply participants 102 with reports 130 and create, using additional input, additional action directives 132, wherein the reports 130 and action directives 132 uniquely aggregate data from the pathology collections 126.

Figure 14:
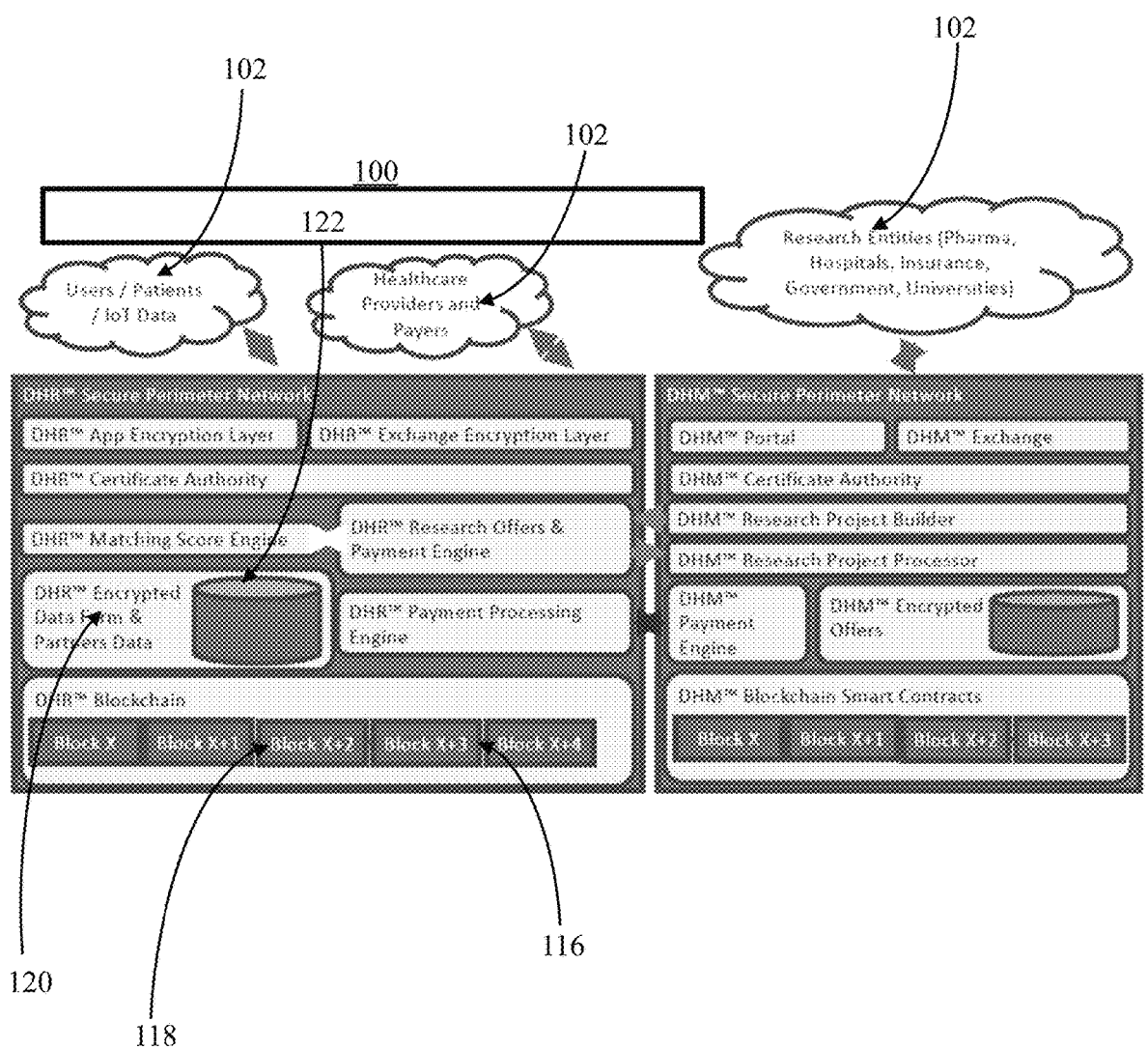
FIG. 14 is an illustration of a digital health marketplace.

FIG. 14 depicts an illustrative embodiment of the present invention, wherein the interface 128 of the system 100 is further configured to allow the participant 102 to view offers presented by other participants 102 based on pathology collections, decentralized ledger blocks 118 and structured data thereof for an aggregation of anonymized participants 102, wherein aggregation and anonymization are controlled by structured data in the secure chain 116.

Figure 15:
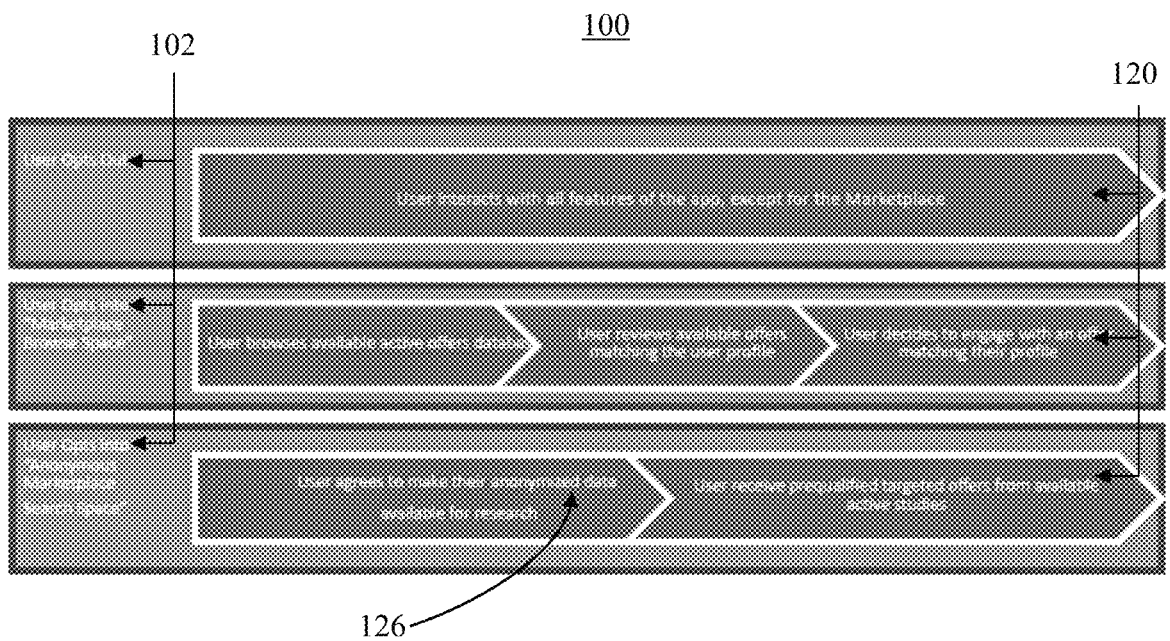
FIG. 15 is an illustration of a digital health marketplace function.

FIG. 15 further depicts an illustrative embodiment wherein the method 600 for carrying out operation of the system 100 includes additional steps for participants 102 to control the settings to view offers presented by other participants 102 including health research offers. The ability of the participant 102 to control the use of their digital health record data contained within the secure chain 116, including access by third party participants 102 subject to governance by the gatekeeper 124, ensures timely and fair compensation for the data shared. The participant can agree or refuse to take part in a marketplace by using the interface 128, application, and system 100 to a) opt out of marketplace; b) opt in to browse available active offers and then decide if/when to engage with an offers database and investigate if there are any research projects with participant 102 selection criteria matching the participant 102 profile that may be parsed from the secure chain 116 or generated as a pathology collection 126; c) opt in to an anonymous marketplace search space where the participant 102 makes their anonymized data available for matching to receive prequalified targeted offers from available active research projects.

Figure 16:
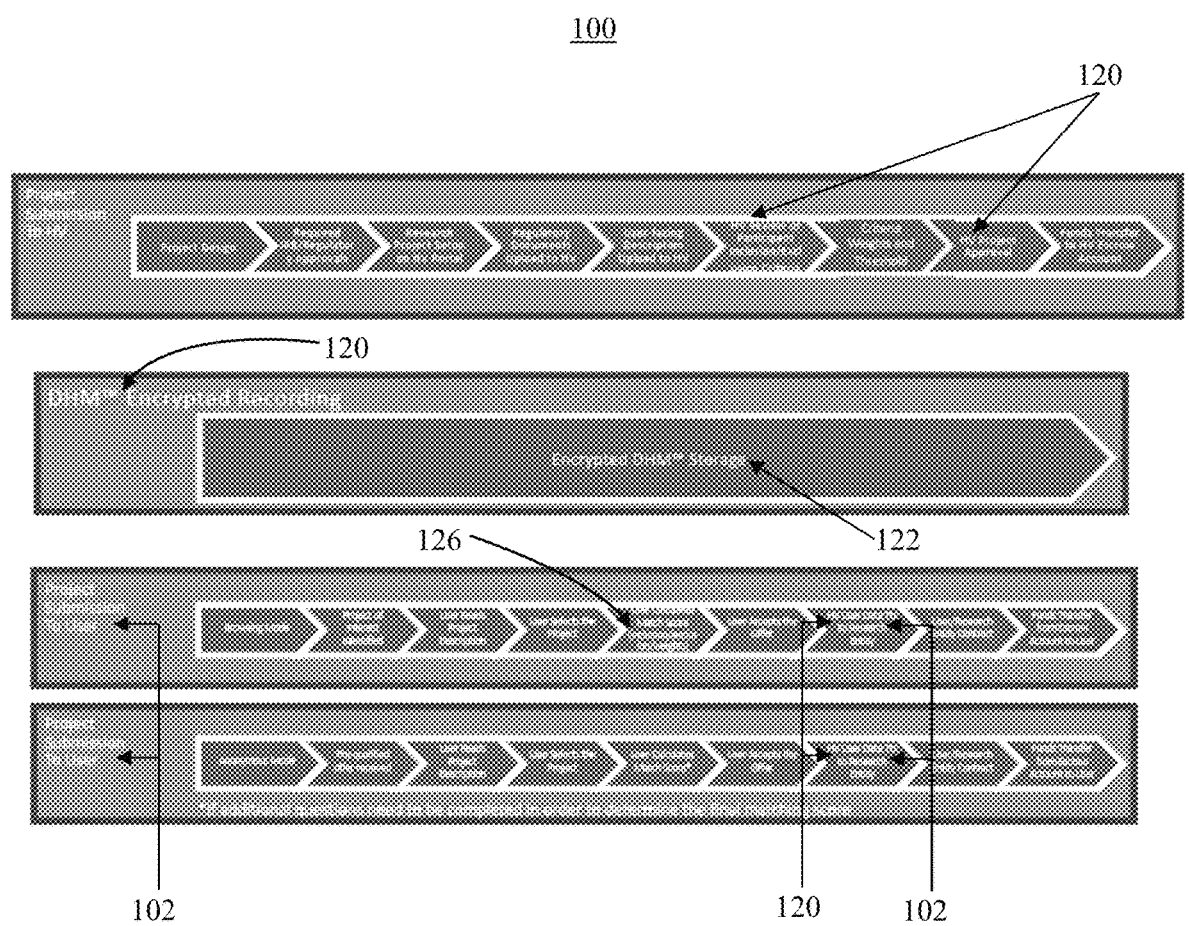
FIG. 16 is an illustration of a digital health marketplace function.
Figure 17A:
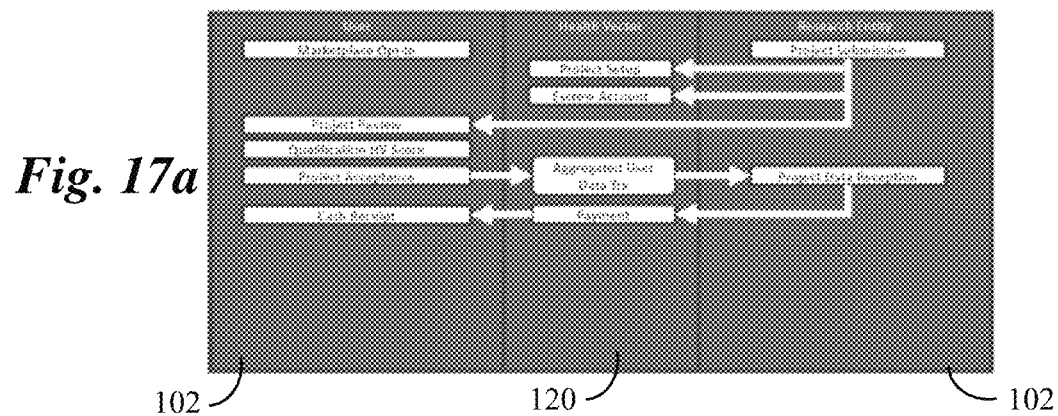
FIGS. 17a-d are illustrations of digital health marketplace interactions.
Figure 17B:
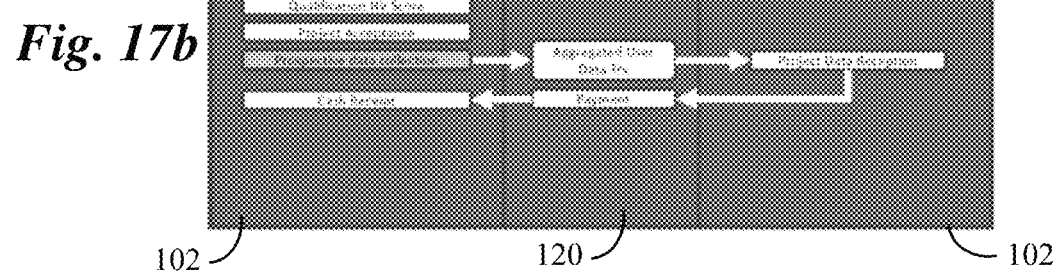
Figure 17C:
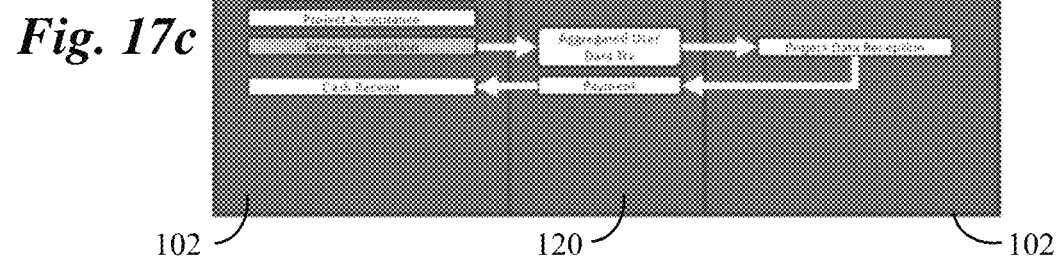
Figure 17D:
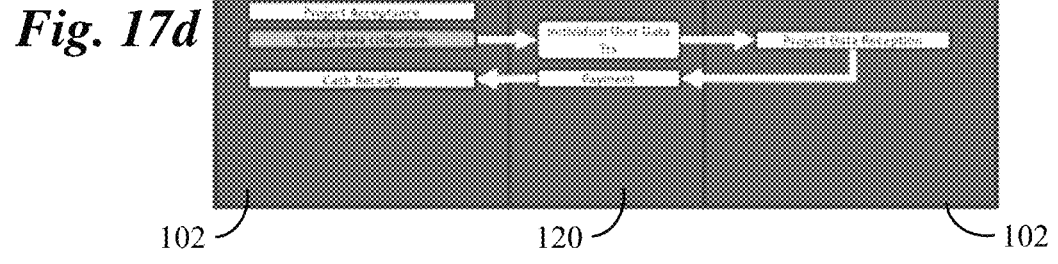
Figure 18:
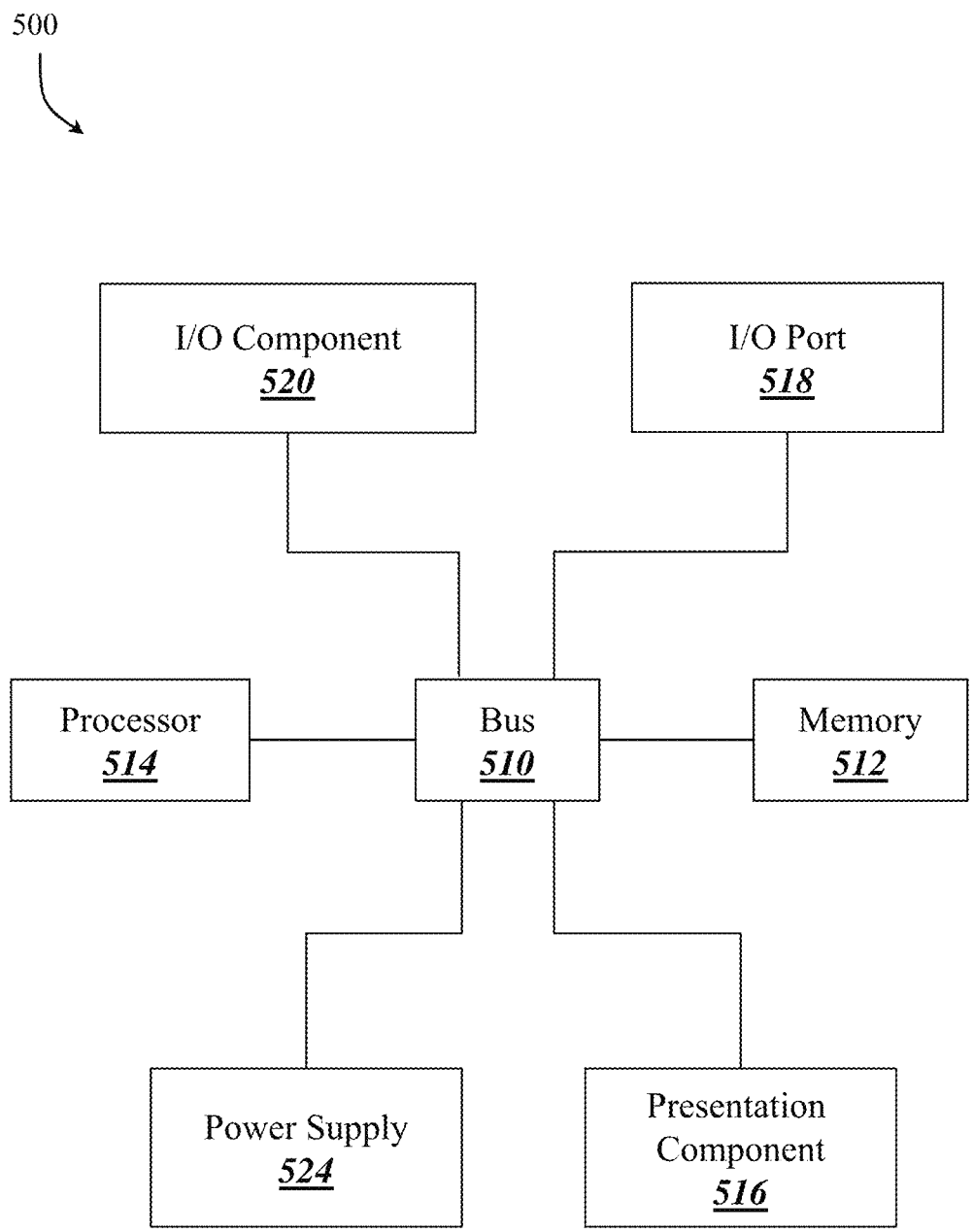
FIG. 18 is a diagram of system physical components.

FIG. 16 depicts an illustrative embodiment of the present invention, the method 600 for carrying out operation of the system 100 includes additional steps for a research entity to provide a research project offer to a potential research project participant 102. Providing a platform for research entities for reaching potential research project participants 102, for offering fair compensation to the participants 102 for the data provided for clinical trials, for the time spent on research activities, while maintaining the anonymity, privacy, and security of the participants' 102 data. First, a research entity designs a research project proposal and obtains approval from an internal review board to conduct research under the proposed specifications. If additional approvals are required (e.g., FDA, EMA, other regulatory bodies), the research entity obtains such approvals. After the required regulatory approvals are obtained, the research project is set up on a system 100 network 120 portal. Through the setup process, research protocol, supporting documents, and the approval documentation are uploaded by the research entity to the application portal. The research entity specifies the desired number of participants 102 to be recruited into the project and prepares a short participant-facing description of the project which includes: type, goal, timeline, duration, participant 102 activities, an estimate of the time commitment expected from the participants 102, and compensation amounts and/or schedules. System 100 administrators review the project specifications and, together with the research entity, establish the participant 102 selection criteria. The participant 102 selection criteria are made up of inclusion factors and their thresholds, exclusion factors, and criteria weights. Once approved, the project funds for participant 102 reimbursement are transferred from the research entity accounts into the escrow account the of the system 100 administrator. The funds are dispersed to participants 102 after completion of each predetermined project milestone and at the end of the project. At the end of the project, unused funds are returned to the research entity. Fees may be paid to the system 100 administrator upon approval of project. The selection criteria are made up of the fields available through the application and relating to demographics, health, and fitness. The research entity can add custom questions to the standard set of fields in the system 100 portal that may be multiple-choice and may include the selection criteria. In a match formula builder, all fields derived from questions can be used to define inclusions and exclusions criteria using logical operators. The formulas can be also weighted in the calculation of a final score. The research entity is able to view aggregate demographics, health and/or fitness data of potential participants 102 under the condition that the potential participants 102 have reviewed and accepted the research project offer provided by the research entity. The selection criteria can be indicated by the research entity, but not used for data gathering. Only the information indicating a match will be provided back. FIGS. 17*a-d* depict exemplary embodiments related to research projects available through the marketplace that demonstrate the interaction of participants 102 with other participants 102 using the network 120 to perform functions related to research projects of different types. Research projects available through the marketplace may be anonymous research projects including: retrospective studies, prospective surveillance studies, and one-time surveys or non-anonymous research projects including: virtual clinical research and in-person clinical research. Retrospective anonymous studies rely on the aggregate data already collected within the system 100 portal—demographics, health, and fitness. Matching scores may be calculated either through the aggregate data only, or in combination with additional information collected from the potential participants 102 via questions submitted by requesting participants 102 and approved by the network 120 and network administrators as part of a research project offer submission, wherein requesting participants 102 may include research entities. After the matching scores for potential participants 102 are calculated and the participants 102 accept the offer to take part in the research project, their aggregate data, derived from the secure chain 116 of decentralized ledger blocks 118 as one or more pathology collections 126, are transmitted to the research entity. Each participant 102 receives payment for their data upon completion of the data transfer. Prospective surveillance anonymous studies rely on aggregate data collected from the participants 102, starting from the moment participants 102 are enrolled in the project and until the project termination date specified in the approved protocol. The matching score could be calculated either through the aggregate data only, or in combination with additional information collected from the potential participants 102 via questions. Data collected includes data (demographics, health, and/or fitness) and additional information obtained from the participants 102 via questionnaires. Each participant 102 receives payment for their data upon completion of the data transfer. One-time anonymous survey studies rely on aggregate data collected from the participants 102 once as part of a survey project. The matching score could be calculated either through the aggregate secure chain 116 data only, or in combination with additional information collected from the potential participants 102 via questions. The data collected may include secure chain 116 data (demographics, health, and/or fitness) and will include the information obtained from the participants 102 via the survey. Each participant 102 receives payment for their data upon completion of the data transfer. Virtual clinical research non-anonymous studies rely on data which cannot be collected in aggregate from individual participants 102. For example, saliva samples, blood samples, measurements collected via various devices (e.g., heart rate monitor, pulse oximeter), administration of medications may be collected for this type of research projects. The data collection toolkits will be mailed to the participants 102 who will be requested to return their samples to the researchers. This type of research is referred to as "virtual", since the participants 102 will not be required to leave their homes in order to participate in the projects. This type of research is referred to as "non-anonymous", since the participants' 102 identifiable information (e.g., name, date of birth, address, etc.) is subject to disclosure. The matching score could be calculated either through the aggregate secure chain 116 data only, or in combination with additional information collected from the potential participants 102 via questions. Each participant 102 receives payment for their data upon completion of the data transfer. In-person clinical research non-anonymous studies rely on data which cannot be collected in aggregate from individual participants 102. For example, saliva samples, blood samples, measurements collected via various devices (e.g., heart rate monitor, pulse oximeter), administration of medications, ingestion of certain foods, endurance measurement, etc. may be collected for this type of research projects. The participants 102 will be requested to visit a research entity location closest to their place of residence and fulfill the requirements of the project as indicated in the approved research protocol. The data collected may also include secure chain 116 data (demographics, health, fitness). Research participants 102 will be compensated for each visit to the research entity location in the amount specified in the approved research protocol or will receive the full compensation amount upon completion of the project. The system 100 protects a fair market value for the use of their data.

In an illustrative embodiment of the present invention, the method 600 for carrying out operation of the system 100 includes additional steps to match a research entity with a potential participant 102 in a research project. The marketplace matches potential participants 102 with research projects and provides compensation to the participants 102 who agree to participate and complete either a pre-determined milestone or project. The participant 102 data are encrypted and not shared with research entities until the time the participant 102 accepts the offer; then the data are shared with the research entity in accordance with the agreement. A participant 102 opens an offer and reads the description of the research goal, type of project, and proposed payment. If interested, the participant 102 can manually generate a score calculated based on secure chain 116 data match. If additional information is needed to determine a match between the potential participant 102 and the project, the potential participant 102 is presented with a questionnaire. Completing the questionnaire produces the final matching score which is displayed to the potential participant 102. If the participant 102 matches the selection criteria of the project, they are presented with project milestones and activities in the research project, as well as the buttons to accept or reject the offer. If the potential participant 102 accepts the offer, they enter a binding agreement. Depending on the type of research project, the participant 102 can, during the selection process, read more information about the type of data that are being shared with the research entity, for what purpose, and for how long. Upon completion of the project or at well-defined milestones, the participant 102 receives payment.

In an illustrative embodiment of the present invention, the method 600 for carrying out operation of the system 100 includes additional steps for establishing smart agreements between different participants 102, wherein said participants 102 may include research entities that are participants 102 in the system 100. Establishing a smart agreement includes the system 100 parsing structured data in the secure chain 116 of decentralized ledger blocks 118 and identifying structured data that conflicts with and/or does not meet requirements of the research project input into action directives 132, wherein prior executed agreements and prior participation in research projects is evaluated. The system 100 converts structured data stored in pathology collections 126 into agreement terms by insertion of the structured data and related action directives 132, input by a requesting participant 102, that may include at least one research entity, into agreement data stored in the network 120 of secure processing devices 122. The system 100 inserts research project parameters, input by requesting participant 102, into agreement terms, wherein each block contains the project details, purpose, data requirements, selection criteria, and compensation levels, as well as anonymous participant 102 data, and the User/participant ID. The requesting participant 102 approves a final form of agreement terms and the system 100, using at least one interface 128, presents the final form of agreement terms to the two or more participants 102 including the at least one requesting participant 102 and the at least one potential participant 102. These parties execute the agreement between two or more participants 102, wherein each respective participant 102 supplies consent and acceptance by input into an interface 128 and application transferring data to the network 120 of secure processing devices 122. Modifying, using structured data stored in the newly generated agreement terms blocks, access privileges controlled by the gatekeeper and directed to the requesting participant 102, yielding access to additional structured data contained within the secure chain of decentralized blocks comprising the digital health record of the potential participant 102. The agreements between potential participants 102 and the research entity requesting participants 102 are stored securely, using one or more additional decentralized ledger blocks 118 residing in the network 120 of secure processing devices 122, to store the agreement terms, consent and acceptance between two or more participants 102, thereby adding to the secure chain 116 of decentralized ledger blocks 118 and creating an additional immutable record for subsequent integration and tracking (wherein each block contains the project details, purpose, data requirements, selection criteria, and compensation levels, as well as anonymous participant 102 data, and User/participant ID), wherein data are encrypted, immutable, and stored in distributed format in the secure chain of decentralized ledger blocks representing a digital health marketplace.

FIG. 15 illustrates an example of a computing device 500 for implementing illustrative systems 100 and methods 600 of the present invention. The computing device 500 is merely an illustrative example of a suitable computing environment and in no way limits the scope of the present invention. Computing devices such as computing device 500 can be implemented as system 100 components such as one of the one or more symptom collecting devices 110, one of the one or more secure processing devices 122, or the functional implementation of the interface 128 used by a system 100 participant 102. In specific embodiments, one or more diagnostic acquisition devices 104 may comprise a computing device 500 as well as other diagnostic equipment specifically designed, configured and programed to perform specific diagnosis acquisition tasks. A "computing device," as represented by FIG. 15, can include a "workstation," a "server," a "laptop," a "desktop," a "hand-held device," a "mobile device," a "tablet computer," or other computing devices, as would be understood by those of skill in the art. Given that the computing device 500 is depicted for illustrative purposes, embodiments of the present invention may utilize any number of computing devices 500 in any number of different ways to implement a single embodiment of the present invention. Accordingly, embodiments of the present invention are not limited to a single computing device 500, where the one or more settlement devices 12, one or more symptom collecting devices 110, one or more secure processing devices 122, or one or more functional implementations of interfaces 128 may all be examples of a computing device 500, as would be appreciated by one with skill in the art, nor are they limited to a single type of implementation or configuration of the example computing device 500.

The computing device 500 can include a bus 510 that can be coupled to one or more of the following illustrative components, directly or indirectly: a memory 512, one or more processors 514, one or more presentation components 516, input/output ports 518, input/output components 520, and a power supply 524. One of skill in the art will appreciate that the bus 510 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 15 is merely illustrative of an exemplary computing device that can be used to implement one or more embodiments of the present invention, and in no way limits the invention.

The computing device 500 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 500.

The memory 512 can include computer-storage media in the form of volatile and/or nonvolatile memory. The memory 512 may be removable, non-removable, or any combination thereof. Exemplary hardware devices are devices such as hard drives, solid-state memory, optical-disc drives, and the like. The computing device 500 can include one or more processors that read data from components such as the memory 512, the various I/O components 520, etc. A graphical user interface may be used in conjunction with the various I/O components 520. Presentation component(s) 516 present data indications to a participant 102 or other device. Exemplary presentation components include a display device, speaker, printing component, vibrating component, etc.

The I/O ports 518 can allow the computing device 500 to be logically coupled to other devices, such as I/O components 520. Some of the I/O components 520 can be built into the computing device 500. Examples of such I/O components 520 include a microphone, joystick, recording device, game pad, satellite dish, scanner, printer, wireless device, networking device, and the like.

One of skill in the art will appreciate a wide variety of ways to modify and alter the integrated longitudinal condition tracking system 100 of FIG. 1, as well as the various components with which it interacts. For example, the network 120 can be implemented according to any number of suitable network structures or architectures. Furthermore, the integrated longitudinal condition tracking may not be limited to health care implementations and alternative embodiments can be used to track education, credit, criminal history, or professional development and licensure events related to participants 102. Additionally, although the components of FIG. 1 are depicted as discrete blocks and elements, in fact the system 100 may be implemented in such a way that multiple of the depicted modules, engines, or other components are implemented with just a single module, engine, or component. Similarly, in some embodiments it may be desirable to implement the system 100 using multiple iterations of the depicted modules, engines, and/or other components, as would be appreciated by one of skill in the art. Furthermore, while some modules and components are depicted as included within the system 100, it should be understood that, in fact, any of the depicted modules alternatively can be excluded from the system 100 and included in a different system. One of skill in the art will appreciate a variety of other ways to expand, reduce, or otherwise modify the system 100 upon reading the present specification.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art. The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one or the entire group members are present in, employed in or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications and other reference materials referenced herein to describe the background of the invention and to provide additional detail regarding its practice are hereby incorporated by reference.

While certain compositions, devices and methods of the present invention have been described with specificity in accordance with certain embodiments, the examples serve only to illustrate the methods and compositions of the invention and are not intended to limit the same.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method for integrated longitudinal condition tracking, the method comprising:
    performing diagnosis acquisition tasks related to a participant using a diagnosis acquisition device;
    generating, using the diagnosis acquisition device, an encrypted diagnosis event block that corresponds to each of the diagnosis acquisition tasks performed and stores diagnosis data in structured data units;
    capturing, using a symptom collecting device, symptom information related to a participant;
    generating, using the symptom collecting device, an encrypted symptom event block that stores symptom data in structured data units;
    verifying, then storing, and linking, using a secure chain of decentralized ledger blocks, decentralized chains of encrypted diagnosis event blocks and encrypted symptom event blocks for a participant based on structured data, wherein the encrypted diagnosis event blocks and encrypted symptom event blocks of the secure chain are immutable;
    managing, using a gatekeeper, encryption and access to the secure chain based on authority granted to the gatekeeper and recorded in the secure chain, wherein the gatekeeper possesses authority to grant and deny access to subsets of the secure chain by participants, wherein access is controlled by configuring sets of structured data; and
    storing, using a network of secure processing devices, secure chains of decentralized ledger blocks comprising encrypted diagnosis event blocks and encrypted symptom event blocks from participants;
    performing data integration tasks, using a network of secure processing devices, by migrating along longitudinal paths of the secure chain, parsing decentralized ledger blocks using structured data embedded in the decentralized ledger blocks, wherein structured data embedded in the decentralized ledger blocks controls access to encrypted diagnosis event blocks and encrypted symptom event blocks based on access granted by the gatekeeper;
    generating, using a network of secure processing devices, pathology collections of encrypted diagnosis event blocks and encrypted symptom event blocks based on sets of parsed structured data, wherein pathology collections are configured based on input from a participant, subject to access granted to the participant by the gatekeeper; and
    providing an interface to supply participants with reports and action directives aggregating data from the pathology collections;
    approving access to pathology collections, unstructured data and structured stored in decentralized ledger blocks and the network of secure processing devices related to participants participating in a digital health marketplace based on submissions of at least one requesting participant, the approving comprising:

providing the at least one requesting participant with access to a network portal displayed using an interface of a system for integrated longitudinal condition tracking;

receiving, from the at least one requesting participant accessing the network portal using the interface, a request to set up a research project offer submission on a digital health marketplace residing within the network of secure processing devices;

receiving, from the at least one requesting participant accessing the network portal using the interface, identification information linking the research project offer submission to structured data stored in a secure chain of decentralized ledger blocks and the network of secure processing devices belonging to the requesting participant;

receiving, from the at least one requesting participant, research project parameters for setting up a research project designed by one or more requesting participants, wherein research project parameters comprise inclusion criteria, exclusion criteria, threshold criteria, time criteria, criteria weighting, compensation data for participants, compensation account data, and offer data to be presented to participants including type of research and research goal;

storing research project parameters and the request to set up a research project offer submission in the network of secure processing devices, wherein project parameters are encrypted;

receiving, from the at least one requesting participant, evidence of approval, wherein evidence of approval comprises uploading to the network of secure processing devices, using the interface, one or more of the group consisting of internal approval, regulatory approval, and prior network administrator approval;

reviewing, by the network of secure processing devices and network administrators, the stored research project parameters, evidence of approval, network data and laws, rules and regulations governing research projects;

providing to the at least one requesting participant, by the interface, an approval decision;

transferring funds, based upon the approval decision and research project parameters, using compensation account data, into an escrow account managed by the network of secure processing devices to be distributed by the network of secure processing devices to participants completing milestones in research project participation;

publishing, the research project offer in the digital health marketplace using the interface and the network of secure processing devices, and storing the research project offer in a database related to the digital health marketplace that is indexed and searchable; and updating structured data, encrypted blocks, access controls, access privileges, privacy restrictions and security restrictions stored in the secure chain of decentralized ledger blocks and the network of secure processing devices managed the network, and network administrators based on the approval decision.

2. The method of claim 1, further comprising:

receiving, from a participant using an interface of a system for integrated longitudinal condition tracking, a selection of one of the group consisting of non-participation in a digital health marketplace, consent to participate in browsing services allowing said participant to browse offers from available active research projects published on the digital health marketplace, and consent to search space services for matching to receive prequalified targeted offers from available active research projects;

wherein participation in browsing services comprises the participant electing when to engage with said offers stored in a database related to the digital health marketplace to determine whether research project parameters match structured data of the participant;

wherein search space services anonymize participant structured data, aggregate participant structured data and make participant structured data available to requesting participants for matching to receive prequalified targeted offers from available active research projects according to submitted research project parameters;

wherein research projects comprise one or more of the group consisting of anonymous retrospective studies, anonymous prospective surveillance studies, anonymous one-time surveys or non-anonymous virtual clinical research and non-anonymous in-person clinical research;

updating structured data, encrypted blocks, access controls, access privileges, privacy restrictions and security restrictions stored in the secure chain of decentralized ledger blocks and the network of secure processing devices managed by the gatekeeper, the network, and network administrators based on the selection made by the participant; and configuring the interface to display a set of data related to the digital health marketplace, browsing services, and search space services authorized by the selection made by the participant.

3. The method of claim 2, further comprising:

receiving, from at least one participant, a request to match research project parameters of a research project offer to a subset of the structured and unstructured data stored in a secure chain of decentralized ledger blocks belonging to a potential participant that the at least one participant is authorized to access based upon the structured data, encrypted blocks, access controls, access privileges, privacy restrictions and security restrictions stored in the secure chain of decentralized ledger blocks and the network of secure processing devices managed by the gatekeeper, the network, and network administrators;

executing action directives anonymizing data and aggregating data from pathology collections of the participant subject to the request to match, according to the research project parameters, migrating along longitudinal paths of the secure chain, parsing decentralized ledger blocks using structured data embedded in the decentralized ledger blocks, performing data integration, and collecting relevant pathology collections;

generating a score indicating an aggregated match of the potential participant to research project parameters calculated based on pathology collections; and presenting, via the interface, a score assessing the volunteer participant, to the at least one participant.

4. The method of claim 3, further comprising:

inserting research project parameters, input by at least one requesting participant, into agreement terms;

converting structured data stored in pathology collections into agreement terms by insertion of the structured data and related action directives, input by at least one requesting participant, into agreement data stored in the network of secure processing devices;

parsing, structured data in the secure chain of decentralized ledger blocks and identifying structured data that do not match the research project parameters input into action directives, wherein prior executed agreements and prior participation in research projects is evaluated;

approving, using input by requesting participant, a final form of agreement terms;

presenting, using at least one interface, the final form of agreement terms to two or more participants including the at least one requesting participant and the potential participant;

executing, the agreement between two or more participants, wherein each respective participant supplies consent and acceptance by input into the interface and application thereby transferring data to the network of secure processing devices;

modifying, using structured data stored in the newly generated agreement terms blocks, structured data, encrypted blocks, access controls, access privileges, privacy restrictions and security restrictions stored in the secure chain of decentralized ledger blocks and the network of secure processing devices managed by the gatekeeper, the network, and network administrators, yielding access to additional structured data contained within the secure chain of decentralized blocks comprising a digital health record of the potential participant; and storing, using one or more additional decentralized ledger blocks residing in the network of secure processing devices, the agreement terms, consent and acceptance between two or more participants, thereby adding to the secure chain of decentralized ledger blocks and creating an additional immutable record for subsequent integration and tracking, wherein data are encrypted, immutable, and stored in distributed format in the secure chain of decentralized ledger blocks representing a digital health marketplace.

* * * * *